(12) United States Patent
Roelle et al.

(10) Patent No.: US 10,514,657 B2
(45) Date of Patent: Dec. 24, 2019

(54) SELECTION METHOD FOR ADDITIVES IN PHOTOPOLYMERS

(71) Applicant: Bayer MaterialScience AG, Monheim Am Rhein (DE)

(72) Inventors: Thomas Roelle, Leverkusen (DE); Friedrich-Karl Bruder, Krefeld (DE); Thomas Fäcke, Leverkusen (DE); Marc-Stephan Weiser, Leverkusen (DE); Dennis Hönel, Zülpich-Wichterich (DE); Christian Diedrich, Düsseldorf (DE)

(73) Assignee: Covestro Deutschland AG, Leverkusen (DE)

( * ) Notice: Subject to any disclaimer, the term of this patent is extended or adjusted under 35 U.S.C. 154(b) by 636 days.

(21) Appl. No.: 14/693,999

(22) Filed: Apr. 23, 2015

(65) Prior Publication Data

US 2015/0277374 A1 Oct. 1, 2015
US 2016/0231705 A9 Aug. 11, 2016

Related U.S. Application Data

(63) Continuation of application No. 13/504,307, filed as application No. PCT/EP2010/066593 on Nov. 2, 2010, now abandoned.

(30) Foreign Application Priority Data

Nov. 3, 2009 (EP) .................................... 09013764

(51) Int. Cl.
| | | |
|---|---|---|
| *G16C 10/00* | (2019.01) | |
| *G16C 20/30* | (2019.01) | |
| *G03F 7/00* | (2006.01) | |
| *G03F 7/004* | (2006.01) | |
| *G06F 7/548* | (2006.01) | |
| *G03F 7/035* | (2006.01) | |
| *G03H 1/02* | (2006.01) | |
| *G11B 7/24044* | (2013.01) | |
| *G11B 7/245* | (2006.01) | |
| *G03H 1/04* | (2006.01) | |
| *G11B 7/0065* | (2006.01) | |

(52) U.S. Cl.
CPC ............... *G03H 1/02* (2013.01); *G03F 7/001* (2013.01); *G03F 7/0046* (2013.01); *G03H 1/04* (2013.01); *G06F 7/548* (2013.01); *G11B 7/245* (2013.01); *G11B 7/24044* (2013.01); *G16C 10/00* (2019.02); *G16C 20/30* (2019.02); *G03F 7/035* (2013.01); *G03H 2001/0264* (2013.01); *G03H 2260/12* (2013.01); *G11B 7/0065* (2013.01)

(58) Field of Classification Search
None
See application file for complete search history.

(56) References Cited

U.S. PATENT DOCUMENTS

| | | | | |
|---|---|---|---|---|
| 4,123,413 A | * | 10/1978 | Mark ..................... | C08K 5/205 524/171 |
| 6,403,702 B1 | * | 6/2002 | Markusch .......... | C08G 18/0895 524/198 |
| 2002/0152038 A1 | | 10/2002 | Sonnenberg et al. | |
| 2003/0008788 A1 | | 1/2003 | Sonnenberg et al. | |
| 2005/0259303 A1 | | 11/2005 | Setthachayanon et al. | |

FOREIGN PATENT DOCUMENTS

| | | |
|---|---|---|
| DE | 10065443 A1 | 7/2002 |
| EP | 0223587 A1 | 5/1987 |
| EP | 1091267 A2 | 4/2001 |
| JP | 2007101681 A | 4/2007 |
| WO | WO-2002051263 A1 | 7/2002 |
| WO | WO-2008/125229 A1 | 10/2008 |

OTHER PUBLICATIONS

Klamt et al. Fluid Phase Equilibria 172, 43-72, 2000.*
Wang et al. Fluid Phase Equilibria 276 (2009) 37-45.*
Wang et al., "Fluid Phase Equilibria", 276, 37-45 (2009).
International Search Report for PCT/EP2010/066593 dated Apr. 6, 2011.

* cited by examiner

*Primary Examiner* — Michael L Borin
(74) *Attorney, Agent, or Firm* — Drinker Biddle & Reath LLP

(57) ABSTRACT

The invention relates to a method for selecting compounds which can be used as additives in photopolymer formulations for producing light holographic media, and to photopolymer formulations which contain at least one softener which are selected according to the claimed method. The invention also relates to the use of photopolymer formulations for producing holographic media.

11 Claims, 5 Drawing Sheets

SELECTION METHOD FOR ADDITIVES IN PHOTOPOLYMERS

CROSS-REFERENCE TO RELATED APPLICATIONS

This application is a divisional application of U.S. patent application Ser. No. 13/504,302, filed May 29, 2012, which is a national stage application (under 35 U.S.C. § 371) of PCT/EP2010/066593, filed Nov. 2, 2010, which claims benefit of European application 09013764.7, filed Nov. 3, 2009, both of which are incorporated herein by reference in their entirety for all their useful purposes.

The invention relates to a method for selecting compounds which can be used as additives in photopolymer formulations for the production of light holographic media, and photopolymer formulations which contain at least one plasticizer which was selected by the method according to the invention.

WO 2008/125229 A1 describes photopolymer formulations of the type mentioned at the outset. These comprise polyurethane-based matrix polymers, acrylate-based writing monomers and photoinitiators. In the cured state, the writing monomers and the photoinitiators are embedded with spatial distribution in the polyurethane matrix. The WO document likewise discloses the addition of dibutyl phthalate, a classical plasticizer for industrial plastics, to the photopolymer formulation.

For uses of photopolymer formulations in the fields of use described below, the refractive index modulation Δn produced by the holographic exposure in the photopolymer plays the decisive role. During the holographic exposure, the interference field of signal and reference light beam (in the simplest case the two plane waves) is mapped by the local photopolymerization of, for example, highly refracting acrylates at sites of high intensity in the interference field into a refractive index grating. The refractive index grating in the photopolymer (the hologram) contains all information of the signal light beam. By illuminating the hologram only with the reference light beam, the signal can then be reconstructed. The strength of the signal thus reconstructed in relation to the strength of the reference light used is referred to as diffraction efficiency, DE below. In the simplest case of a hologram which forms from the superposition of two plane waves, the DE is obtained from the quotient of the intensity of the light diffracted on reconstruction and the sum of the intensities of incident reference light and diffracted light. The higher the DE, the more efficient is a hologram with respect to the necessary quantity of reference light which is required for making the signal visible with a fixed brightness. Highly refractive acrylates are capable of producing refractive index gratings having a high amplitude between regions having the lowest refractive index and regions having the highest refractive index and hence of permitting holograms having a high DE and high Δn in photopolymer formulations. It should be noted that the DE is dependent on the product of Δn and the photopolymer layer thickness d. The larger the product, the greater is the possible DE (for reflection holograms). The width of the angular range in which the hologram is visible (reconstructed), for example on monochromatic illumination, depends only on the layer thickness d. On illumination of the hologram with, for example, white light, the width of the spectral range which can contribute to the reconstruction of the hologram likewise depends only on the layer thickness d. It is true that the smaller d is the greater are the respective acceptance widths. It is therefore intended to produce bright and easily visible holograms, a high Δn·d and a small thickness d should be strived for in particular so that DE is as large as possible. This means that the higher Δn is, the more latitude is achieved for configuring bright holograms by adjusting d and without loss of DE. The optimization of Δn on the optimization of photopolymer formulations is therefore of outstanding importance (ref. Hariharan Optical Holography).

One possibility for achieving as large a Δn as possible is the use of photopolymer formulations which contain plasticizers having no optical refraction, i.e. those having a low refractive index. In addition to the optical properties, a further important selection criterion for such plasticizers is that they must have sufficiently low volatility under typical production conditions for photopolymer formulations. Owing to an observed loss of mass in the production of the holographic film media, an obvious presumption is that evaporation of individual components might occur during the production, especially in the area of drying. However, on consideration of the boiling points and of the vapour pressures of the components used, it was not expected that these should be a cause for the evaporation at the respective drying temperatures and hence a reason for the substantially lower Δn values.

However, the vapour pressure is a parameter with the aid of which the suitability of components for use in the industrial production of holographic media cannot be tested. This is because the vapour pressure of a chemical compound is a physical constant which describes how a pure substance or a mixture of substances is in thermodynamic equilibrium with its liquid or solid phase. For dynamic systems, however, the vapour pressure provides no guidance.

Thus, the vapour pressure does not describe the situation which prevails, for example, in a continuously operated coating unit in which the material applied with a small layer thickness, distributed over a large surface by air circulation which ensures that the gaseous phase is constantly removed, is dried.

Expediently, the volatility is considered instead of the vapour pressure. Since this value is difficult to determine experimentally, theoretical methods could be readily applied for this purpose.

Methods in which, based on simple molecular descriptors, relationships between the molecular properties and the physical properties of substance, referred to below as Quantitative Structure Property Relationships (QSPR), are sought and known in principle from the literature. Thus, for example, Ha et al. (Energy & Fuels, 19, 152, (2005)) describe QSPR models which are suitable for estimating boiling points, relative densities and refractive indices of saturated and aromatic hydrocarbons without heteroatoms. Liu et al. have presented a QSPR model which is suitable primarily for fluorine and sulphur-containing hydrocarbons (J. Micro/Nanolith. MEMS MOEMS 7, 023001-1-023001-11, (2008)). These models are derived on the basis of a large set of experimental data and frequently permit a high degree of predictability for compounds which are sufficiently similar to the substances used for the preparation but have a significantly reduced accuracy when the similarity is not present.

Further known methods for estimating molecular properties are group contribution methods which divide the given molecule into "groups" to which a certain incremental contribution to a given physical property is assigned. The physical properties are then obtained by summing the group contributions. An example is the method published in 2001 by Marrero and Gani (Fluid Phase Equilib. 183-184, 183-

208 (2001)). However, a principle problem of this method is the fact that it is not possible to treat compounds whose molecular structure contains groups not covered by the method. Moreover, the accuracy is typically not sufficient for quantitative conclusions.

WO 02/051263 and DE 10065443 describe QSPR methods which are based on descriptors derived from quantum chemical calculations. The method is used there to describe the phase behaviour of aromas or fragrances in multimaterial systems. These descriptors are suitable in particular for describing a versatile set of molecules, so that it is possible to find QSPR models with very few descriptors which can be used in a versatile manner.

BRIEF DESCRIPTION OF EMBODIMENTS

It was an object of the present invention to provide a selection method for additives in photopolymer formulations which permit production of holograms having a relatively high brightness.

The object is achieved, in the method according to the invention if the refractive index and the volatility, expressed as TGA95 value, of a given still uncharacterized substance is estimated with the aid of a mathematical method in order to assess the suitability thereof as an additive in photopolymer formulations. A substance is considered to be suitable if its refractive index estimated by the method according to the invention is ≤1.4600 and its estimated TGA95 value is >100° C.

For assessing the vaporization properties of a component with a small layer thickness during a drying process on open surfaces, the consideration of the volatility of this chemical component is important and is a measure of the tendency to evaporate. This volatility can preferably be determined by a thermogravimetric analysis (TGA).

The TGA95 value of the individual components are then determined by weighing an amount of about 10 mg of the sample of the respective component into an aluminium pan having a volume of 70 µl, introducing the aluminium pan an oven of a thermobalance, preferably of a TG50 thermobalance from Mettler-Toledo, and measuring the loss of mass of the sample in the open aluminium pan at a constant oven heating rate of 20 K/min, the starting temperature being 30° C. and the end temperature of the oven 600° C., flushing the oven with a 200 ml/min nitrogen stream during the determination for determining as the TGA 95 value of the respective component, the temperature at which a loss of mass of the sample of 5% by weight, based on the originally weighed in amount of the sample, has occurred.

In order to use the selection method according to the invention, first a substance to be tested is chosen (step a), a three-dimensional structure of which is created with the aid of a suitable software package. This structure is then subjected to a conformer analysis in a manner known per se with the aid of a force field method in order to determine the conformers of the substance which have the lowest energy (step b). The number of conformers is then further reduced by further optimization of the geometry by a force field method and a subsequent similarity analysis (step c). Steps a-c can be carried out, for example, with the conformers module of the Materials Studio programme package from Accelrys.

The conformers generated in steps a-c are then optimized in terms of geometry by quantum chemical methods, ideally the B-P86 density functional and a triple ζ valence basis being used (step d). The optimization of the geometry is effected with the use of the continuum solvation model Conductor like Screening Model (COSMO), the element-specific COSMO radii optimized by Klamt being used if possible (AIChE Journal, 48, 369, (2002); Fluid Phase Equilibria, 172, 43 (2000); J. Chem. Soc. Perkin Trans. II, 799 (1993)). If elements for which no such optimized radii are available are present in the molecule, 1.17 times the Bondi valence radius is assumed.

On the basis of the COSMO radii, a cavity outside which the molecule is ideally electrostatically shielded from the environment during the optimization of the geometry is calculated by the quantum chemistry software used. The surface (in Å$^2$) and the volume of this cavity (in Å$^3$) are in each case descriptors in the context of the method according to the invention (step e).

The third descriptor is derived from the shielding charge surface of the geometrically optimized molecule, which is obtained in the quantum chemical optimization of the geometry with COSMO. The surface is divided with the aid of a suitable computer programme, such as, for example, the COSMOtherm programme of COSMOlogic, into segments whose mean shielding charge density (σ) is calculated. The third descriptor is then finally obtained as the second moment (M$^2$) of the frequency distribution (P(σ)), the surface shielding charge densities of these segments (step f):

$$M^2 = 10 \cdot \sum_i P(\sigma_i) \cdot \sigma_i^2 \cdot \Delta\sigma,$$

where Δσ is the interval width with which the discrete frequency distribution was generated. The charge densities σ are stated in the unit e/nm$^2$.

The calculation of the descriptors A, V and M$^2$ used in the method according to the invention, carried out in the manner described, is effected in an identical manner for all conformers taken into account. Subsequently, the individual descriptors of the conformers are averaged according to their weight in the Boltzmann distribution (step g). The Boltzmann factors are determined using the energies which were obtained as the result of the quantum chemical optimization of the geometry by COSMO.

Finally with the descriptors determined in this manner, the refractive index and the volatility of the substance to be tested are estimated. For this purpose, the molar polarizability (MP) of the compound to be tested is first determined with the aid of a QSPR approach known from the literature, for example by one of the methods of Crippen et al. (J. Comput. Chem., 7, 565, (1986) or Chem. Inf. Comput. Sci. 39, 868, (1999)). The volatility (TGA95) is estimated according to the invention on the basis of the QSPR approach (step h):

$$TGA95 \approx 207.015 \cdot \frac{M^2}{A} + 41.405 \cdot \sqrt[3]{V} - 253.2$$

The density is estimated according to the invention according to a second QSPR approach using (step i):

$$\rho = 0.89 \cdot \frac{M}{V \cdot N_A} - 0.2 \cdot \frac{A}{V} + 0.01 \cdot \sqrt{M^2}$$

and used to calculate the refractive index at 589 nm ($n_D^{20}$) with the aid of the Lorentz-Lorenz equation (step j):

$$n_D = \sqrt{\frac{2 \cdot \frac{\rho \cdot MP}{M} + 1}{1 - \frac{\rho \cdot MP}{M}}}$$

In the last step, the suitability of the substance as an additive in photopolymer formulations is assessed according to the estimated $n^{20};_D$ and TGA95 value (step k).

Suitable compounds in the context of the method according to the invention have a refractive index of ≤1.4600 and a TGA95 value of ≥100° C.

BRIEF DESCRIPTION OF THE DRAWINGS

The foregoing brief description, as well as the following detailed description, may be better understood when read in conjunction with the appended drawings. For the purpose of assisting in the explanation of the invention, there are shown in the drawings representative embodiments which are considered illustrative. It should be understood, however, that the invention is not limited in any manner to the precise arrangements and instrumentalities shown.

In the drawings.

DETAILED DESCRIPTION OF EMBODIMENTS

Preferred Embodiments

Figure 1:
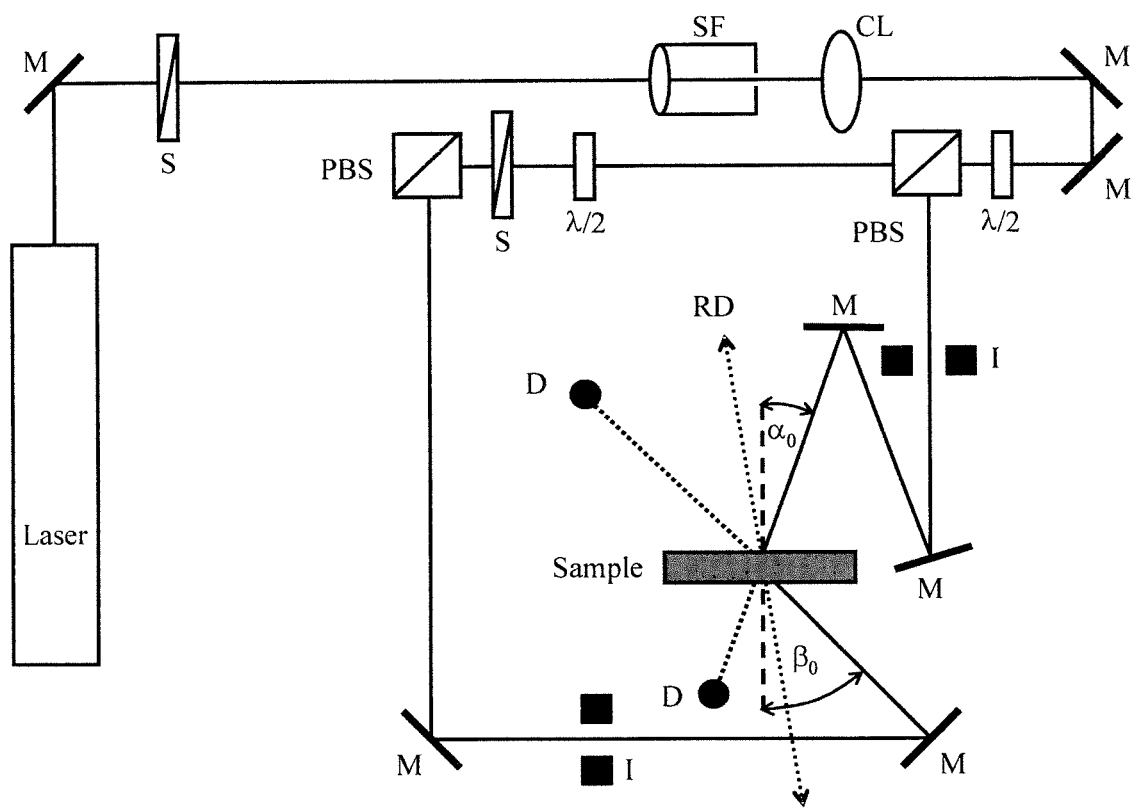
FIG. 1 illustrates a holographic experimental setup with which the diffraction efficiency (DE) of the media was measured
Figure 2:
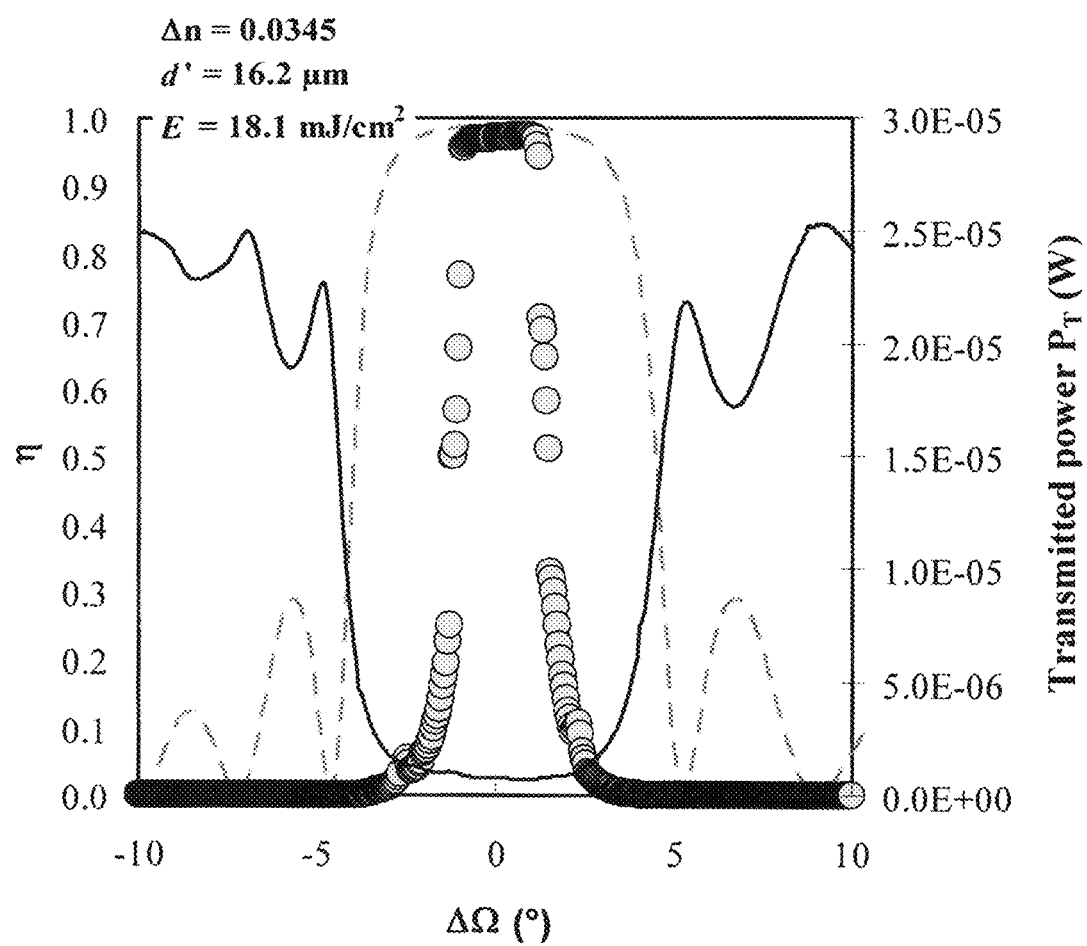
FIG. 2 illustrates a graph showing the measured data of the diffraction efficiency, the theoretical Bragg curve and the transmitted intensity plotted against the angle detuning.

According to a first embodiment, the conformer with the lowest energy which is found in the conformer analysis, preferably all conformers which are up to 4 kJ/mol and particularly preferably all conformers which are up to 8 kJ/mol above the lowest conformer, are taken into account for the method.

In a particularly preferred embodiment of the method according to the invention, a check is carried out in step k) to determine whether the volatility of the compound to be tested is >120° C. and the refractive index $n^{20};_D$ thereof is ≤1.4500, preferably ≤1.4400, particularly preferably ≤1.4300.

A further aspect of the invention relates to a photopolymer formulation comprising matrix polymers, writing monomers and photoinitiators, said photopolymer formulation containing at least one plasticizer which is selected by the method according to the invention.

The matrix polymers may be in particular polyurethanes. Preferably, the polyurethanes are obtained by reacting an isocyanate component a) with an isocyanate-reactive component b).

The isocyanate component a) preferably comprises polyisocyanates. Polyisocyanates which may be used are all compounds well known to the person skilled in the art or mixtures thereof, which on average have two or more NCO functions per molecule. These may have an aromatic, araliphatic, aliphatic or cycloaliphatic basis. In minor amounts, it is also possible concomitantly to use monoisocyanates and/or polyisocyanates containing unsaturated groups.

For example, butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate, the isomeric bis(4,4'-isocyanatocyclohexyl)methanes and mixtures thereof having any desired isomer content, isocyanatomethyl-1,8-octane diisocyanate, 1,4-cyclohexylene diisocyanate, the isomeric cyclohexanedimethylene diisocyanates, 1,4-phenylene diisocyanate, 2,4- and/or 2,6-toluylene diisocyanate, 1,5-naphthylene diisocyanate, 2,4'- or 4,4'-diphenylmethane diisocyanate and/or triphenylmethane 4,4',4"-triisocyanate.

The use of derivatives and monomeric di- or triisocyanates having urethane, urea, carbodiimide, acylurea, isocyanurate, allophanate, biuret, oxadiazinetrione, uretdione and/or iminooxadiazinedione structures is likewise possible.

The use of polyisocyanates based on aliphatic and/or cycloaliphatic di- or triisocyanates is preferred.

The polyisocyanates of component a) are particularly preferably dimerized or oligomerized aliphatic and/or cycloaliphatic di- or triisocyanates.

Isocyanurates, uretdiones and/or iminooxadiazinediones based on HDI, 1,8-diisocyanato-4-(isocyanatomethyl)octane or mixtures thereof are very particularly preferred.

NCO-functional prepolymers having urethane, allophanate, biuret and/or amide groups can likewise be used as component a). Prepolymers of component a) are obtained in a manner well known per se to the person skilled in the art by reacting monomeric, oligomeric or polyisocyanates a1) with isocyanate-reactive compounds a2) in suitable stoichiometry with optional use of catalysts and solvents.

Suitable polyisocyanates a1) are all aliphatic, cycloaliphatic, aromatic or araliphatic di- and triisocyanates know per se to the person skilled in the art, it being unimportant whether these were obtained by means of phosgenation or by phosgene-free processes. In addition, the higher molecular weight secondary products of monomeric di- and/or triisocyanates having a urethane, urea, carbodiimide, acylurea, isocyanurate, allophanate, biuret, oxadiazinetrione, uretdione or iminooxadiazinedione structure, which are known per se to the person skilled in the art, can also be used, in each case individually or as any desired mixtures with one another.

Examples of suitable monomeric di- or triisocyanates which can be used as component a1) are butylene diisocyanate, hexamethylene diisocyanate (HDI), isophorone diisocyanate (IPDI), trimethylhexamethylene diisocyanate (TMDI), 1,8-diisocyanato-4-(isocyanatomethyl)octane, isocyanatomethyl-1,8-octane diisocyanate (TIN), 2,4- and/or 2,6-toluene diisocyanate.

OH-functional compounds are preferably used as isocyanate-reactive compounds a2) for the synthesis of the prepolymers. These are analogous to the OH-functional compounds as described below for the component b).

The use of amines for the prepolymer preparation is also possible. For example, ethylenediamine, diethylenetriamine, triethylenetetramine, propylenediamine, diaminocyclohexane, diaminobenzene, diaminobisphenyl, difunctional polyamines, such as, for example, Jeffamine®, amine-terminated polymers having number average molar masses of up to 10 000 g/mol or any desired mixtures thereof with one another are suitable.

For the preparation of prepolymers containing biuret groups, isocyanate is reacted in excess with amine, a biuret group forming. Suitable amines in this case for the reaction with the di-, tri- and polyisocyanates mentioned are all oligomeric or polymeric, primary or secondary, difunctional amines of the abovementioned type.

Preferred prepolymers are urethanes, allophanates or biurets of aliphatic isocyanate-functional compounds and oligomeric or polymeric isocyanate-reactive compounds having number average molar masses of 200 to 10 000 g/mol; urethanes, allophanates or biurets of aliphatic isocyanate-functional compounds and oligomeric or polymeric polyols or polyamines having number average molar masses of 500 to 8500 g/mol are particularly preferred and allophanates of HDI or TMDI and difunctional polyetherpolyols having number average molar masses of 1000 to 8200 g/mol are very particularly preferred.

The prepolymers described above preferably have residual contents of free monomeric isocyanate of less than 1% by weight, particularly preferably less than 0.5% by weight, very particularly preferably less than 0.2% by weight.

Of course, the isocyanate component may contain further isocyanate components proportionately in addition to the prepolymers described. Aromatic, araliphatic, aliphatic and cycloaliphatic di-, tri- or polyisocyanates are suitable for this purpose. It is also possible to use mixtures of said di-, tri- or polyisocyanates. Examples of suitable di-, tri- or polyisocyanates are butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate (TMDI), the isomeric bis(4,4'-isocyanatocyclo-hexyl)methanes and mixtures thereof having any desired isomer content, isocyanatomethyl 1,8-octane diisocyanate, 1,4-cyclohexylene diisocyanate, the isomeric cyclohexanedimethylene diisocyanates, 1,4-phenylene diisocyanate, 2,4- and/or 2,6-toluylene diisocyanate, 1,5-naphthylene diisocyanate, 2,4'- or 4,4'-diphenylmethane diisocyanate, triphenylmethane 4,4',4"-triisocyanate or derivatives thereof having a urethane, urea, carbodiimide, acylurea, isocyanurate, allophanate, biuret, oxadiazinetrione, uretdione, iminooxadiazinedione structure and mixtures thereof. Polyisocyanates based on oligomerized and/or derivatized diisocyanates which were freed from excess diisocyanate by suitable methods, in particular those of hexamethylene diisocyanate, are preferred. The oligomeric isocyanurates, uretdiones and iminooxadiazinediones of HDI and mixtures thereof are particularly preferred.

It is optionally also possible for the isocyanate component a) proportionately to contain isocyanates which are partly reacted with isocyanate-reactive ethylenically unsaturated compounds. α,β-Unsaturated carboxylic acid derivatives, such as acrylates, methacrylates, maleates, fumarates, maleimides, acrylamides, and vinyl ethers, propenyl ethers, allyl ethers and compounds which contain dicyclopentadienyl units and have at least one group reactive towards isocyanates are preferably used here as isocyanate-reactive ethylenically unsaturated compounds; these are particularly preferably acrylates and methacrylates having at least one isocyanate-reactive group. Suitable hydroxy-functional acrylates or methacrylates are, for example, compounds such as 2-hydroxyethyl (meth)acrylate, polyethylene oxide mono(meth)acrylates, polypropylene oxide mono(meth) acrylates, polyalkylene oxide mono(meth)acrylates, poly(ε-caprolactone) mono(meth)acrylates, such as, for example, Tone® M100 (Dow, USA), 2-hydroxypropyl (meth)acrylate, 4-hydroxybutyl (meth)acrylate, 3-hydroxy-2,2-dimethylpropyl (meth)acrylate, the hydroxy-functional mono-, di- or tetra(meth)acrylates of polyhydric alcohols, such as trimethylolpropane, glycerol, pentaerythritol, dipentaerythritol, ethoxylated, propoxylated or alkoxylated trimethylolpropane, glycerol, pentaerythritol, dipentaerythritol or the industrial mixtures thereof. In addition, isocyanate-reactive oligomeric or polymeric unsaturated compounds containing acrylate and/or methacrylate groups are suitable alone or in combination with the abovementioned monomeric compounds. The proportion of isocyanates which are partly reacted with isocyanate-reactive ethylenically unsaturated compounds, based on the isocyanate component a) is 0 to 99%, preferably 0 to 50%, particularly preferably 0 to 25% and very particularly preferably 0 to 15%.

It is optionally also possible for the abovementioned isocyanate component a) completely or proportionately to contain isocyanates, which are completely or partly reacted with blocking agents known to the person skilled in the art from coating technology. The following may be mentioned as an example of blocking agents: alcohols, lactams, oximes, malonic esters, alkyl acetoacetates, triazoles, phenols, imidazoles, pyrazoles and amines, such as, for example, butanone oxime, diisopropylamine, 1,2,4-triazole, dimethyl-1,2,4-triazole, imidazole, diethyl malonate, ethyl acetoacetate, acetone oxime, 3,5-dimethylpyrazole, ε-caprolactam, N-tert-butylbenzylamine, cyclopentanone carboxyethyl ester or any desired mixtures of these blocking agents.

All polyfunctional, isocyanate-reactive compounds which have on average at least 1.5 isocyanate-reactive groups per molecule can in principle be used as component b).

Isocyanate-reactive groups in the context of the present invention are preferably hydroxy, amino or thio groups; hydroxy compounds are particularly preferred.

Suitable polyfunctional, isocyanate-reactive compounds are, for example, polyester-, polyether-, polycarbonate-, poly(meth)acrylate- and/or polyurethanepolyols.

Suitable polyesterpolyols are, for example, linear polyesterdiols or branched polyester polyols, as are obtained in a known manner from aliphatic, cycloaliphatic or aromatic di- or polycarboxylic acids or their anhydrides with polyhydric alcohols having an OH functionality of ≥2.

Examples of such di- or polycarboxylic acids or anhydrides are succinic, glutaric, adipic, pimelic, suberic, azelaic, sebaccic, nonanedicarboxylic, decanedicarboxylic, terephthalic, isophthalic, o-phthalic, tetrahydrophthalic, hexahydrophthalic or trimellitic acid and acid anhydrides such as o-phthalic, trimellitic or succinic anhydride, or any desired mixtures thereof with one another.

Examples of such suitable alcohols are ethanediol, di-, tri- and tetraethylene glycol, 1,2-propanediol, di-, tri- and tetrapropylene glycol, 1,3-propanediol, 1,4-butanediol, 1,3-butanediol, 2,3-butanediol, 1,5-pentanedial, 1,6-hexanediol, 2,2-dimethyl-1,3-propanediol, 1,4-dihydroxycyclohexane, 1,4-dimethylolcyclohexane, 1,8-octanediol, 1,10-decanediol, 1,12-dodecanediol, trimethylolpropane, glycerol or any desired mixtures thereof with one another.

The polyesterpolyols may also be based on natural or raw materials, such as castor oil. It is also possible for the polyesterpolyols to be based on homo- or copolymers of lactones, as can preferably be obtained by an addition reaction of lactones or lactone mixtures, such as butyrolactone, ε-caprolactone and/or methyl-ε-caprolactone, with hydroxy-functional compounds, such as polyhydric alcohols having an OH functionality of ≥2, for example of the abovementioned type.

Such polyesterpolyols preferably have number average molar masses of 400 to 4000 g/mol, particularly preferably of 500 to 2000 g/mol. Their OH functionality is preferably 1.5 to 3.5, particularly preferably 1.8 to 3.0.

Suitable polycarbonatepolyols are obtainable in a manner known per se by reacting organic carbonates or phosgene with diols or diol mixtures.

Suitable organic carbonates are dimethyl, diethyl and diphenyl carbonate.

Suitable diols or mixtures comprise the polyhydric alcohols mentioned per se in connection with the polyester segments and having an OH functionality of ≥2, preferably 1,4-butanediol, 1,6-hexanediol and/or 3-methylpentanediol, or polyesterpolyols can be converted into polycarbonatepolyols.

Such polycarbonatepolyols preferably have number average molar masses of 400 to 4000 g/mol, particularly preferably of 500 to 2000 g/mol. The OH functionality of these polyols is preferably 1.8 to 3.2, particularly preferably 1.9 to 3.0.

Suitable polyetherpolyols are polyadducts of cyclic ethers with OH- or NH-functional starter molecules, said polyadducts optionally having a block structure.

Suitable cyclic ethers are, for example, styrene oxides, ethylene oxide, propylene oxide, tetrahydrofuran, butylene oxide, epichlorohydrin and any desired mixtures thereof.

Starters which may be used are the polyhydric alcohols mentioned per se in connection with the polyesterpolyols and having an OH functionality of ≥2 and primary or secondary amines and amino alcohols.

Preferred polyetherpolyols are those of the abovementioned type, exclusively based on propylene oxide, or random or block copolymers based on propylene oxide with further 1-alkylene oxides, the proportion of the 1-alkylene oxide not being higher than 80% by weight. In addition, poly(trimethylene oxides) and mixtures of the polyols mentioned as being preferred are preferred. Propylene oxide homopolymers and random or block copolymers which have oxyethylene, oxypropylene and/or oxybutylene units are particularly preferred, the proportion of oxypropylene units, based on the total amount of all oxyethylene, oxypropylene and oxybutylene units, accounting for at least 20% by weight, preferably at least 45% by weight. Here, oxypropylene and oxybutylene comprise all respective linear and branched C3- and C4-isomers.

Such polyetherpolyols preferably have number average molar masses of 250 to 10 000 g/mol, particularly preferably of 500 to 8500 g/mol and very particularly preferably of 600 to 4500 g/mol. The OH functionality is preferably 1.5 to 4.0, particularly preferably 1.8 to 3.1.

In addition, aliphatic, araliphatic or cycloaliphatic di-, tri- or polyfunctional alcohols which have a low molecular weight, i.e. having molecular weights of less than 500 g/mol, and a short chain, i.e. containing 2 to 20 carbon atoms, are also suitable as polyfunctional, isocyanate-reactive compounds as constituents of component c).

These may be, for example, ethylene glycol, diethylene glycol, triethylene glycol, tetraethylene glycol, dipropylene glycol, tripropylene glycol, 1,2-propanediol, 1,3-propanediol, 1,4-butanediol, neopentylglycol, 2-ethyl-2-butylpropanediol, trimethylpentanediol, positional isomers of diethyloctanediol, 1,3-butylene glycol, cyclohexanediol, 1,4-cyclohexanedimethanol, 1,6-hexanediol, 1,2- and 1,4-cyclohexanediol, hydrogenated bisphenol A (2,2-bis(4-hydroxycyclohexyl)propane), 2,2-dimethyl-3-hydroxypropionic acid (2,2-dimethyl-3-hydroxypropyl ester). Examples of suitable triols are trimethylolethane, trimethylolpropane or glycerol. Suitable higher-functional alcohols are ditrimethylolpropane, pentaerythritol, dipentaerythritol or sorbitol.

One or more photoinitiators are used as component c). These are usually initiators which can be activated by actinic radiation and initiate a polymerization of the corresponding polymerizable groups. Photoinitiators are commercially distributed compounds known per se, a distinction being made between monomolecular (type I) and bimolecular (type II) initiators. Furthermore, these initiators are used for free radical, anionic (or), cationic (or mixed) forms of the abovementioned polymerizations, depending on the chemical nature.

(Type I) systems for the free radical photopolymerization are, for example, aromatic ketone compounds, e.g. benzophenones, in combination with tertiary amines, alkylbenzophenones, 4,4'-bis(dimethylamino)benzophenone (Michlers ketone), anthrone and halogenated benzophenones or mixtures of said types. (Type II) initiators, such as, benzoin and its derivatives, benzil ketals, acylphosphine oxides, e.g. 2,4,6-trimethylbenzoyl-diphenylphosphine oxide, bisacylophosphine oxides, phenylglyoxylic esters, campherquinone, alpha-aminoalkylphenones, alpha-, alpha-dialkoxyacetophenones, 1-[4-(phenylthio)phenyl]octane-1,2-dione 2-(O-benzoyloxime), differently substituted hexarylbisimidazoles (HABI) with suitable coinitiators, such as, for example, mercaptobenzoxazole and alpha-hydroxyalkylphenones are furthermore suitable. The photoinitiator systems described in EP-A 0223587 and consisting of a mixture of an ammonium aryl borate and one or more dyes can also be used as a photoinitiator. For example, tetrabutylammonium triphenylhexylborate, tetrabutylammonium triphenylbutylborate, tetrabutylammonium trinaphthylbutylborate, tetramethylammonium triphenylbenzylborate, tetra(n-hexyl)ammonium (sec-butyl)triphenylborate, 1-methyl-3-octylimidazolium dipentyldiphenylborate, tetrabutylammonium tris(4-tert-butyl)phenylbutylborate, tetrabutylammonium tris(3-fluorophenyl)hexylborate and tetrabutylammonium tris(3-chloro-4-methylphenyl)hexylborate are suitable as the ammonium aryl borate. Suitable dyes are, for example, new methylene blue, thionine, basic yellow, pinacynol chloride, rhodamine 6G, gallocyanine, ethylviolet, Victoria blue R, celestine blue, quinaldine red, crystal violet, brilliant green, astrazone orange G, darrow red, pyronine Y, basic red 29, pyrillium I, safranine O, cyanine and methylene blue, azure A (Cunningham et al., RadTech'98 North America UV/EB Conference Proceedings, Chicago, Apr. 19-22, 1998).

The photoinitiators used for the anionic polymerization are as a rule (type I) systems and are derived from transition metal complexes of the first series. Here are chromium salts, such as, for example, trans-$Cr(NH_3)_2(NCS)_4$— (Kutal et al, Macromolecules 1991, 24, 6872) or ferrocenyl compounds (Yamaguchi et al., Macromolecules 2000, 33, 1152). A further possibility of anionic polymerization consists in the use of dyes, such as crystal violet leuconitrile or malchite green leuconitrile, which can polymerize cyanoacrylates by photolytic decomposition (Neckers et al., Macromolecules 2000, 33, 7761). However, the chromophore is incorporated thereby into the polymer so that the resulting polymers are coloured throughout.

The photoinitiators used for the cationic polymerization substantially comprise three classes: aryldiazonium salts, onium salts (here specifically: iodonium, sulphonium and selenonium salts) and organometallic compounds. On irradiation both in the presence and in the absence of a hydrogen donor, phenyldiazonium salts can produced a cation that initiates the polymerization. The efficiency of the overall system is determined by the nature of the counterion used for the diazonium compound. The not very reactive but very expensive $SbF_6^-$, $AsF_6^-$ or $PF_6^{31}$ are preferred here. These compounds are as a rule not very suitable for use in coating of the thin films since the nitrogen liberated after the exposure reduces the surface quality (pinholes) (Li et al., Polymeric Materials Science and Engineering, 2001, 84, 139). Very widely used and commercially available in many forms are onium salts, especially sulphonium and iodonium salts. The photochemistry of these compounds has been investigated for a long time. After excitation, the iodonium salts initially decompose homolytically and thus produce a free radical and a radical anion which is stabilized by H abstraction and releases a proton and then initiates the cationic polymerization (Dektar et al. J. Org. Chem. 1990, 55, 639; J. Org. Chem., 1991, 56, 1838). This mechanism permits the use of iodonium salts also for free radical photopolymerization. The choice of the counterion is once again of considerable importance here; $SbF_6^-$, $AsF_6^-$ or $PF_6^-$ are likewise preferred. Otherwise, this choice of the substitution of the aromatic is completely free in this structure class and is determined substantially by the availability of suitable starting building blocks for the synthesis. The sulphonium salts are compounds which decompose in according to Norrish(II) (Crivello et al., Macromolecules, 2000, 33, 825). In the case of the sulphonium salts, too, the choice of the counterion is of critical importance and manifests itself substantially in the curing rate of the polymers. The best results are as a rule obtained with $SbF_6^-$ salts. Since the self-absorption of iodonium and sulphonium salts is at <300 nm, these compounds must be appropriately sensitized for the photopolymerization with near UV or short-wave visible light. This is effected by the use of more highly absorbing aromatics such as, for example, anthracene and derivatives (Gu et al., Am. Chem. Soc. Polymer Preprints, 2000, 41 (2), 1266) or phenothiazine or derivatives thereof (Hua et al, Macromolecules 2001, 34, 2488-2494).

It may also be advantageous to use mixtures of these compounds. Depending on the radiation source used for the curing, type and concentration of photoinitiator must be adapted in a manner known to a person skilled in the art. Further details are described, for example, in P. K. T. Oldring (Ed.), Chemistry & Technology of UV & EB Formulations For Coatings, Inks & Paints, Vol. 3, 1991, SITA Technology, London, pages 61-328.

Preferred photo initiators c) are mixtures of tetrabutylammonium triphenylhexylborate, tetrabutylammonium triphenylbutylborate, tetrabutylammonium trinaphthylbutylborate, tetrabutylammonium tris-(4-tert-butyl) phenylbutylborate, tetrabutylammonium tris-(3-fluorophenyl)hexyl-borate and tetrabutylammonium tris-(3-chloro-4-methylphenyl)hexylborate with dyes, such as, for example, astrazone orange G, methylene blue, new methylene blue, azure A, pyrillium I, safranine O, cyanine, gallocyanine, brilliant green, crystal violet, ethyl violet and thionine.

The photopolymer formulation may additionally contain urethanes as plasticizers, it being possible for the urethanes preferably to be substituted by at least one fluorine atom.

The urethanes are preferably compounds which have a structural element of the general formula I.

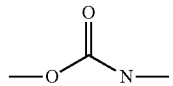

Formula I

They can be obtained from monofunctional alcohols and monofunctional isocyanates. These are preferably substituted by at least one fluorine atom.

It is more preferable if the fluorourethanes have the general formula II

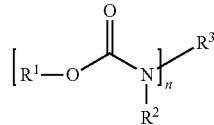

Formula II in which n is ≥1 and n is ≥8 and $R^1$, $R^2$, $R^3$ are hydrogen and/or, independently of one another, linear, branched, cyclic or heterocyclic organic radicals which are unsubstituted or optionally also substituted by heteroatoms, at least one of the radicals $R^1$, $R^2$, $R^3$ being substituted by at least one fluorine atom. Here, $R^1$ is particularly preferably an organic radical having at least one fluorine atom.

According to a further embodiment, $R^1$ may comprise 1-20 $CF_2$ groups and/or one or more $CF_3$ groups, particularly preferably 1-15 $CF_2$ groups and/or one or more $CF_3$ groups, particularly preferably 1-10 $CF_2$ groups and/or one or more $CF_3$ groups, very particularly preferably 1-8 $CF_2$ groups and/or one or more $CF_3$ groups, $R^2$ may comprise a C1-C20 alkyl radical, preferably a C1-C15 alkyl radical, particularly preferably a C1-C10 alkyl radical or hydrogen, and/or $R^3$ may comprise a C1-C20 alkyl radical, preferably a C1-C15 alkyl radical, particularly preferably a C1-C10 alkyl radical or hydrogen.

The fluorourethanes may have a fluorine content of 10-80% by weight of fluorine, preferably of 13-70% by weight of fluorine and particularly preferably 17.5-65% by weight of fluorine.

According to a further preferred embodiment of the invention, it is envisaged that the photopolymer formulation contains 10 to 89.999% by weight, preferably 25 to 70% by weight, of matrix polymers, 10 to 60% by weight, preferably 25 to 50% by weight, of writing monomers, 0.001 to 5% by weight of photoinitiators and optionally 0 to 4% by weight, preferably 0 to 2% by weight, of catalyst, 0 to 5% by weight, preferably 0.001 to 1% by weight, of free radical stabilizers, 0 to 30% by weight, preferably 0 to 25% by weight, of plasticizers and 0 to 5% by weight, preferably 0.1 to 5% by weight, of further additives, the sum of all constituents being 100% by weight.

Photopolymer formulations having 25 to 70% by weight of matrix polymers consisting of compounds of component a) and of component b), 25 to 50% by weight of writing monomers, 0.001 to 5% by weight of photoinitiators, 0 to 2% by weight of catalyst, 0.001 to 1% by weight of free radical stabilizers, optionally 0 to 25% by weight of the urethanes described above and optionally 0.1 to 5% by weight of further additives are particularly preferably used.

A further preferred embodiment of the invention envisages that the photopolymer formulation contains urethanes having a number average molecular weight of ≤250 g/mol, preferably of ≤200 g/mol and particularly preferably of ≤190 g/mol.

The photopolymer formulation therefore advantageously contains aliphatic urethanes. In this case, the aliphatic urethanes may have in particular the general formula (III)

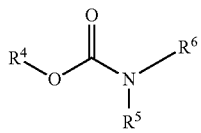
(III)

in which $R^4$, $R^5$, $R^6$, independently of one another, are linear or branched (C1-C20)-alkyl radicals optionally substituted by heteroatoms. It is particularly preferable if $R^4$ is a linear or branched (C1-C8)-alkyl radical, $R^5$ is a linear or branched (C1-C8)-alkyl radical and/or $R^6$ is a linear or branched (C1-C8)-alkyl radical, it being particularly preferable if $R^4$ is a linear or branched (C1-C4)-alkyl radical and $R^5$ is a linear or branched (C1-C6)-alkyl radical and $R^6$ is hydrogen. In this case, it was in fact found that the urethanes thus obtained are very compatible with the polyurethane matrix and show the effect described here.

According to a further preferred embodiment, it is envisaged that the urethanes have substantially no free NCO groups.

The writing monomers can preferably comprise a monofunctional acrylate of the general formula (IV)

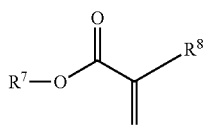
(IV)

in which $R^7$, $R^8$ are hydrogen and/or, independently of one another, linear, branched, cyclic or heterocyclic unsubstituted organic radicals.

It is also possible for the writing monomers to comprise a polyfunctional writing monomer, it being possible for this to be in particular a polyfunctional acrylate.

The polyfunctional acrylate can preferably have the general formula (V)

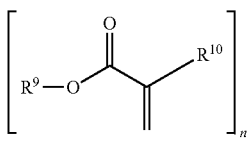
(V)

in which n is ≥2 and n is ≤4 and $R^9$, $R^{10}$ are hydrogen and/or, independently of one another, linear, branched, cyclic or heterocyclic organic radicals which are unsubstituted or optionally also substituted by heteroatoms.

The present invention furthermore relates to the use of a photopolymer formulation according to the invention for the production of holographic media, in particular for the production of in-line holograms, off-axis holograms, full-aperture transfer holograms, white light transmission holograms, Denisyuk holograms, off-axis reflection holograms, edge-lit holograms and holographic stereograms.

EXAMPLES

The invention is explained in more detail below with reference to examples. First, the synthesis and characterization of the example molecules are described and thereafter the handling thereof in the method according to the invention.

Unless noted otherwise, all stated percentages relate to percent by weight.

Determination of the Refractive Index

Measurement of the refractive index $n^{20}{:}_D$ at a wavelength of 589 nm: a sample of the example compound was introduced into an Abbe refractometer and $n^{20}{:}_D$ was measured.

Determination of the Vapour Pressure

Figure 5:
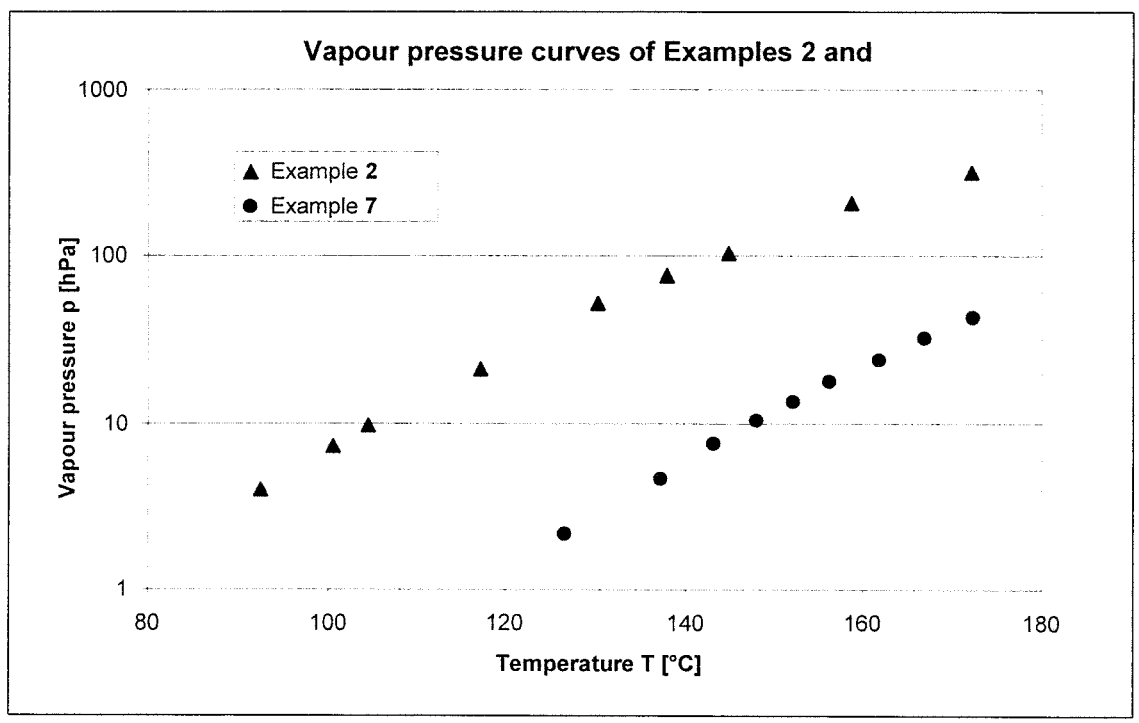
FIG. 5 illustrates a graph showing the vapor pressure curves of Examples 2 and 7.

For Examples 2 and 7, the synthesis of which is described further below, the vapour pressures were determined under a nitrogen atmosphere in a circulation apparatus (isobar in an Ebulliometer) by the Röck method according to the OECD guideline for the testing of chemicals, No. 104. The resulting vapour pressure curves are shown in FIG. 5 in the temperature range from 90 to 180° C. The resulting parameters of the Antoine equation $$lg\frac{P^{Sat}}{hPa} = A - \frac{B}{C + T(° C.)}$$

are accordingly:

TABLE 1

Physical data of Examples 2 and 7

| Example | Parameters of the Antoine equation | | | Vapour pressure at 80° C. [hPa] | Vapour pressure at 100° C. [hPa] | TGA 95 ° C. |
| --- | --- | --- | --- | --- | --- | --- |
| | A | B | C | | | |
| 2 | 15.6189 | 2616.075 | 90.3596 | 1.30 | 7.30 | 72.5 |
| 7 | 6.5466 | 1053.404 | 42.458 | 0.13 | 0.42 | 111.8 |

It is evident from this that the equilibrium vapour pressure, for example for a temperature of 100° C. in both Examples 2 and 7, is <10 hPa, so that it would be expected that the two components have sufficient stability in the formulation. The TGA95 values of the two two Examples 2 and 7 on the other hand correlate substantially better with the observed behaviour during the film coating.

FIG. 1 shows the measured vapour pressure curves of Examples 2 and 7.

Determination of the TGA95 Value

The TGA95 values of the individual components are determined by weighing an amount of about 10 mg of the respective component into an aluminium pan having a volume of 70 µl, introducing the aluminium pan into an oven of a thermobalance, preferably a TG50 thermobalance from Mettler-Toledo, and measuring the loss of mass (of the sample) in the open aluminium pan at a constant oven heating rate of 20 K/min, the starting temperature being 30° C. and the end temperature of the oven being 600° C., the oven being flushed with a 200 ml/min nitrogen stream during the determination and the temperature at which a loss of mass of the sample of 5% by weight, based on the originally weighed in amount of the sample, has occurred being determined as the TGA95 value of the respective component.

Measurement of the Holographic Properties DE and Δn of the Holographic Media by Means of Two-Beam Interference in Reflection Arrangement For the measurement of the holographic performance, the protective foil of the holographic film is peeled off and the holographic film is laminated on the photopolymer side with a 1 mm thick glass plate of suitable length and width using a rubber roller with gentle pressure. This sandwich of glass and photopolymer film can now be used for determining the holographic performance parameters DE and Δn.

The holographic media produced as described below were then tested with regard to the holographic properties by means of a measurement arrangement according to FIG. 3, as follows:

The beam of an He—Ne laser (emission wavelength 633 nm) was converted with the aid of the spatial filter (SF) and together with the collimation lens (CL) into a parallel homogeneous beam. The final cross sections of the signal and reference beam are established by the iris diaphragm (I). The diameter of the iris diaphragm opening is 0.4 cm. The polarization-dependent beam splitters (PBS) split the laser beam into two coherent equally polarized beams. Via the λ/2 plates, the power of the reference beam was adjusted to 0.5 mW and the power of the signal beam to 0.65 mW. The powers were determined using the semiconductor detectors (D) with sample removed. The angle of incidence ($\alpha_0$) of the reference beam is −21.8° and the angle of incidence ($\beta_0$) of the signal beam is 41.8°. The angles are measured starting from the sample normal to the beam direction. According to FIG. 3, $\alpha_0$ therefore has a negative sign and $\beta_0$ a positive sign. At the location of the sample (medium), the interference field of the two overlapping beams produced a grating of lighter and darker strips which are perpendicular to the angle dissectors of the two beams incident on the sample (reflection hologram). The strip spacing Λ, also referred to as grating period, in the medium is ~225 nm (the refractive index of the medium is seen to be ~1.504).

Figure 3:
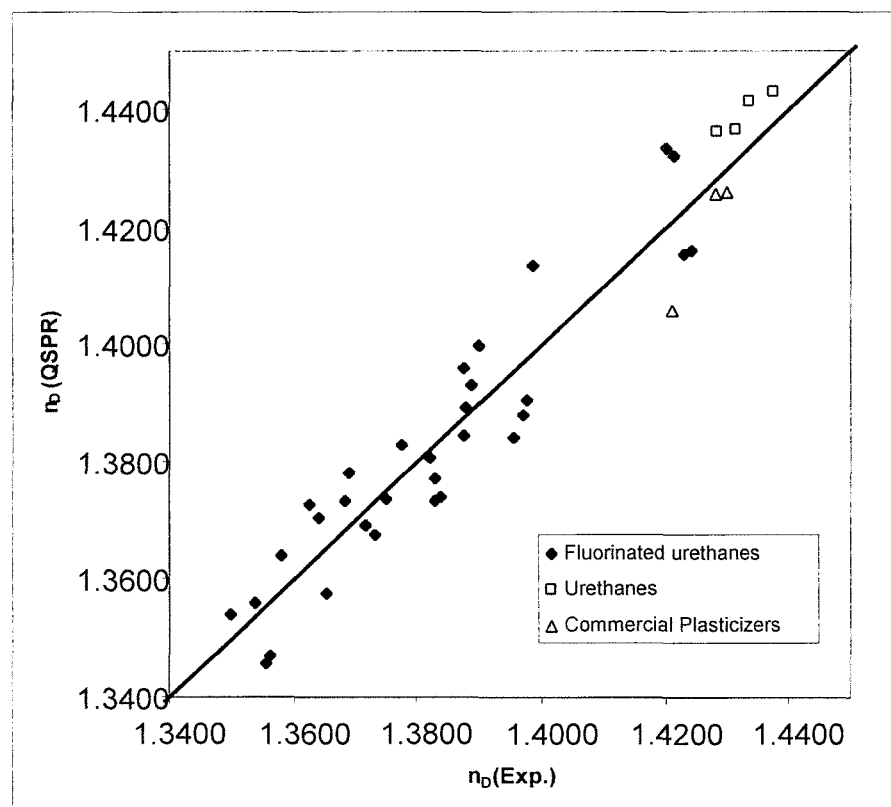
FIG. 3 illustrates a comparison between the experimental refractive indices and TGA95 values of Examples 1-39 and those estimated by the selection method according to an embodiment of the present invention.

FIG. 3 shows the holographic experimental setup with which the diffraction efficiency (DE) of the media was measured.

Holograms were recorded in the medium in the following manner:

both shutters (S) are opened for the exposure time t.

thereafter, with closed shutters (S), the medium was allowed a time of 5 minutes for diffusion of the still unpolymerized writing monomers.

The holograms recorded were now read in the following manner. The shutter of the signal beam remained closed. The shutter of the reference beam was opened. The iris diaphragm of the reference beam was closed to a diameter of <1 mm. This ensured that the beam was always completely in the previously recorded hologram for all angles of rotation (Ω) of the medium. The turntable, now computer controlled, covered the angle range from $\Omega_{min}$ to $\Omega_{max}$ with an angle step width of 0.05°. Ω is measured from the sample normal to the reference direction of the turntable. The reference direction of the turntable is obtained when the angle of incidence of the reference beam and that of the signal beam have the same absolute value during recording of the hologram, i.e. $\alpha_0$=−31.8° and $\beta_0$=31.8°. $\Omega_{recording}$ is then 0°. For $\alpha_0$=−21.8° and $\beta_0$=41.8°, $\Omega_{recording}$ is therefore 10°. In general, the following is true for the interference field during recording of the hologram:

$$\alpha_0 = \theta_0 + \Omega_{recording}$$

$\theta_0$ is the semiangle on the laboratory system outside the medium and the following is true during recording of the hologram:

$$\theta_0 = \frac{\alpha_0 - \beta_0}{2}.$$

In this case, $\theta_0$ is therefore −31.8°. At each angle of rotation approached, the powers of the beam transmitted in the zeroth order were measured by means of the corresponding detector D and the powers of the beam diffracted in the first order were measured by means of the detector D. The diffraction efficiency was obtained at each angle Ω approached as a quotient of:

$$\eta = \frac{P_D}{P_D + P_T}$$

$P_D$ is the power in the detector of the diffracted beam and $P_T$ is the power in the detector of the transmitted beam.

By means of the method described above, the Bragg curve (it describes the diffraction efficiency η as a function of the angle of rotation Ω of the recorded hologram) was measured and was stored in a computer. In addition, the intensity transmitted in the zeroth order was plotted against the angle of rotation Ω and stored in a computer.

The maximum diffraction efficiency (DE=$\eta_{max}$) of the hologram, i.e. its peak value, was determined at $\Omega_{reconstruction}$. It may have been necessary for this purpose to change the position of the detector of the diffracted beam in order to determine this maximum value.

The refractive index Δn and the thickness d of the photopolymer layer was now determined by means of the coupled wave theory (cf. H. Kogelnik, The Bell System Technical Journal, Volume 48, November 1969, Number 9, page 2909-page 2947) from the measured Bragg curve and variation of the transmitted intensity as a function of angle. It should be noted that, owing to the thickness shrinkage occurring as result of the photopolymerization, the strip spacing Λ' of the hologram and the orientation of the strips (slant) may differ from the strip spacing Λ of the interference pattern and the orientation thereof. Accordingly, the angle $\alpha_0$' and the corresponding angle of the turntable $\Omega_{reconstruction}$, at which maximum diffraction efficiency is reached will also differ from $\alpha_0$ and from the corresponding $\Omega_{recording}$, respectively. The Bragg condition changes as a result. This change is taken into account in the evaluation method. The evaluation method is described below:

All geometrical quantities which relate to the recorded hologram and not to the interference pattern are shown as quantities represented by a dashed line.

According to Kogelnik, the following is true for the Bragg curve η(Ω) of reflection hologram:

$$\eta = \begin{cases} \dfrac{1}{1 - \dfrac{1-(\xi v)^2}{\sin^2\left(\sqrt{\xi^2 - v^2}\right)}}, & \text{for } v^2 - \xi^2 < 0 \\[2ex] \dfrac{1}{1 + \dfrac{1-(\xi v)^2}{\sinh^2\left(\sqrt{v^2 - \xi^2}\right)}}, & \text{for } v^2 - \xi^2 \geq 0 \end{cases}$$

with:

$$v = \frac{\pi \cdot \Delta n \cdot d'}{\lambda \cdot \sqrt{|c_s \cdot c_r|}}$$

$$\xi = -\frac{d'}{2 \cdot c_s} \cdot DP$$

$$c_s = \cos(\vartheta') - \cos(\psi') \cdot \frac{\lambda}{n \cdot \Lambda'}$$

$$c_r = \cos(\vartheta')$$

$$DP = \frac{\pi}{\Lambda'} \cdot \left(2 \cdot \cos(\psi' - \vartheta') - \frac{\lambda}{n \cdot \Lambda'}\right)$$

$$\psi' = \frac{\beta' + \alpha'}{2}$$

$$\Lambda' = \frac{\lambda}{2 \cdot n \cdot \cos(\psi' - \alpha')}$$

On reading the hologram ("reconstruction"), the following is true, as shown analogously above:

$\theta'_0 = \theta_0 + \Omega$ $\sin(\theta'_0) = n \cdot \sin(\theta')$

Under the Bragg condition, the "dephasing" DP is 0. Accordingly, the following is true:

$\alpha'_0 = \theta_0 + \Omega_{reconstruction}$ $\sin(\alpha'_0) = n \cdot \sin(\alpha')$ The still unknown angle β' can be determined from the comparison of the Bragg condition of the interference field on recording of the hologram and the Bragg condition on reading the hologram, assuming that only thickness shrinkage takes place. Then follows:

$$\sin(\beta') = \frac{1}{n} \cdot [\sin(\alpha_0) + \sin(\beta_0) - \sin(\theta_0 + \Omega_{reconstruction})]$$

v is the grating thickness, ξ is the detuning parameter and ψ' is the orientation (slant) of the refractive index grating which was recorded. α' and β' correspond to the angles $\alpha_0$ and $\beta_0$ of the interference field on recording of the hologram, but measured in the medium and applicable to the grating of the hologram (after thickness shrinkage). n is the mean refractive index of the photopolymer and was set at 1.504. λ is the wavelength of the laser light in vacuo.

The maximum diffraction efficiency (DE=$\eta_{max}$) is then obtained for ξ=0 as:

$$DE = \tanh^2(v) = \tanh^2\left(\frac{\pi \cdot \Delta n \cdot d'}{\lambda \cdot \sqrt{\cos(\alpha') \cdot \cos(\alpha' - 2\psi)}}\right)$$

Figure 4:
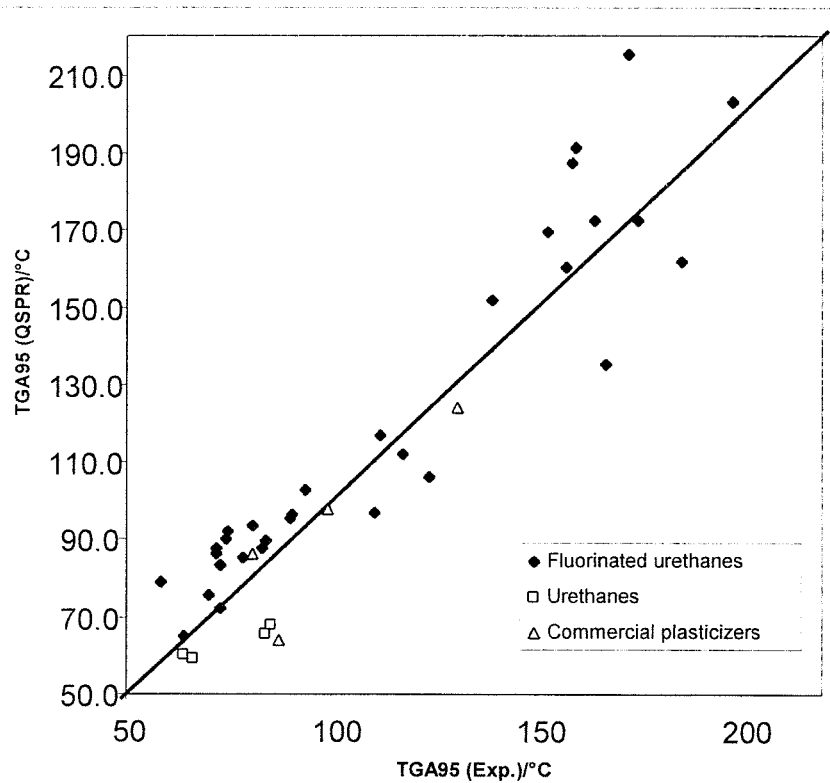
FIG. 4 illustrates a comparison between the experimental refractive indices and TGA95 values of Examples 1-39 and those estimated by the selection method according to an embodiment of the present invention.

The measured data of the diffraction efficiency, the theoretical Bragg curve and the transmitted intensity are, as shown in FIG. 4, plotted against the centred angle of rotation $\Delta\Omega = \Omega_{reconstruction} - \Omega = \alpha'_0 - \theta'_0$, also referred to as angle detuning.

Since DE is known, the shape of the theoretical Bragg curve according to Kogelnik is determined only by the thickness d' of the photopolymer layer. Δn is subsequently corrected via DE for a given thickness d' so that measurement and theory of DE always agree. d' is now adapted until the angle positions of the first secondary minima of the theoretical Bragg curve agree with the angle positions of the first secondary maxima of the transmitted intensity and additionally the full width at half maximum (FWHM) for the theoretical Bragg curve and the transmitted intensity agree.

Since the direction in which a reflection hologram concomitantly rotates on reconstruction by means of an Ω scan, but the detector for the diffracted light can detect only a finite angle range, the Bragg curve of broad holograms (small d') is not completely detected in an Ω scan, but only the central region, with suitable detector positioning. That shape of the transmitted intensity which is complementary to the Bragg curve is therefore additionally used for adapting the layer thickness d'.

FIG. 4 shows the plot of the Bragg curve η according to the coupled wave theory (dashed line), of the measured diffraction efficiency (solid circles) and of the transmitted power (black solid line) against the angle detuning ΔΩ.

For a formulation, this procedure was possibly repeated several times for different exposure times t on different media in order to determine the average energy dose of the incident laser beam at which DE reaches the saturation value during recording of the hologram. The average energy dose E is obtained from the powers of the two part-beams coordinated with the angles $\alpha_0$ and $\beta_0$ (reference beam with $P_r$=0.50 mW and signal beam with $P_s$=0.63 mW), the exposure time t and the diameter of the iris diaphragm (0.4 cm), as follows:

$$E(\text{mJ/cm}^2) = \frac{2 \cdot [P_r + P_s] \cdot t(s)}{\pi \cdot 0.4^2 \text{ cm}^2}$$

The powers of the part-beams were adapted so that the same power density is achieved in the medium at the angles $\alpha_0$ and $\beta_0$ used.

In examples, respectively the maximum value in Δn is reported, and the doses used are between 4 and 64 mJ/cm$^2$ per arm.

Substances Used

CGI-909 (tetrabutylammonium tris(3-chloro-4-methylphenyl)(hexyl)borate, [1147315-11-4]) is an experimental product produced by CIBA Inc., Basle, Switzerland.

The (fluorinated) alcohols and monofunctional isocyanates used were obtained in the chemicals trade.

1,8-Diisocyanato-4-(isocyanatomethyl)octane (TIN) was prepared as described in EP 749958.

2,4,4-Trimethylhexane 1,6-diisocyanate, Vestanat TMDI, is a product of Evonik Degussa GmbH, Marl, Germany.

Preparation of the Polyol Component:

In a 1 l flask, 0.18 g of tin octoate, 374.8 g of ɛ-caprolactone and 374.8 g of a difunctional polytetrahydrofuran-polyetherpolyol (equivalent weight 500 g/mol OH) were initially introduced and heated to 120° C. and kept at this temperature until the solids content (proportion of nonvolatile constituents) was 99.5% by weight or more. Thereafter, cooling was effected and the product was obtained as a waxy solid.

Preparation of Urethane Acrylate 1: phosphorothioyltris (oxybenzene-4,1-diylcarbamoyloxyethane-2,1-diyl) trisacrylate In a 500 ml round-bottomed flask, 0.1 g of 2,6-di-tert-butyl-4-methylphenol, 0.05 g of dibutyltin dilaurate (Desmorapid Z, Bayer MaterialScience AG, Leverkusen, Germany) and and 213.07 g of a 27% strength solution of tris(p-isocyanatophenyl) thiophosphate in ethyl acetate (Desmodur® RFE, product of Bayer MaterialScience AG, Leverkusen, Germany) were initially introduced and heated to 60° C. Thereafter, 42.37 g of 2-hydroxyethyl acrylate were added dropwise and the mixture was further kept at 60° C. until the isocyanate content had fallen below 0.1%. Thereafter, cooling was effected and the ethyl acetate was completely removed in vacuo. The product was obtained as a semicrystalline solid.

Preparation of Urethane Acrylate 2: 2-({[3-(methylsulphanyl)phenyl]carbamoyl}oxy)-ethyl prop-2-enoate):

In a 100 ml round-bottomed flask, 0.02 g of 2,6-di-tert-butyl-4-methylphenol, 0.01 g of Desmorapid® Z, 11.7 g of 3-(methylthio)phenyl isocyanate were initially introduced and heated to 60° C. Thereafter, 8.2 g of 2-hydroxyethyl acrylate were added dropwise and the mixture was further kept at 60° C. until the isocyanate content had fallen below 0.1%. Thereafter, cooling was effected. The product was obtained as a light yellow liquid.

Example 1: Trifluoroethyl Butylcarbamate

In a 2 l round-bottomed flask, 0.50 g of Desmorapid Z and 498 g of n-butyl isocyanate were initially introduced and heated to 60° C. Thereafter, 502 g of trifluoroethanol were added dropwise and the mixture was further kept at 60° C. until the isocyanate content had fallen below 0.1%. Thereafter, cooling was effected. The product was obtained as a colourless solid. The refractive index $n^{20};_D$ determined by method B is 1.3900 and the measured TGA95 value is 63.7° C.

Further Examples

Examples 2-25 were prepared in the manner described for Example 1, in the compositions stated in Table 2. The associated $n^{20};_D$ and TGA95 values for all examples were measured as described in the above correspondingly named sections.

TABLE 2

Preparation and characterization of Examples 2-35

| Example | Name | Isocyanate and amount | Alcohol and amount | Catalyst and amount | Temp [° C.] | Description |
|---|---|---|---|---|---|---|
| 2 | 2,2,2-Trifluoroethyl hexylcarbamate | n-Hexyl isocyanate 55.9 g | Trifluoroethanol 44.0 g | Desmorapid Z 0.05 g | 60° C. | colourless liquid |
| 3 | 2,2,3,3-Tetrafluoropropyl butylcarbamate | n-Butyl isocyanate 10.7 g | 2,2,3,3-Tetra-fluoropropan-1-ol 14.3 g | Desmorapid Z 0.01 g | 60° C. | colourless liquid |
| 4 | Bis(2,2,2-trifluoroethyl)-(2,2,4-trimethylhexane-1,6-diyl) biscarbamate | 2,4,4-Trimethylhexane 1,6-diisocyanate (TMDI) 496 g | Trifluoroethanol 463 g | Desmorapid Z 0.48 G | 60° C. | colourless liquid |
| 5 | Bis(2,2,2-trifluoroethyl)-[4-({[(2,2,2-trifluoroethoxy)-carbonyl]amino}methyl) octane-1,8-diyl] biscarbamate | 1,8-Diisocyanato-4-(iso-cyanatomethyl) octane (TIN) 228 g | Trifluoroethanol 272 g | Desmorapid Z 0.48 g | 60° C. | colourless liquid |
| 6 | 2,2,3,3,4,4,4-Heptafluorobutyl butylcarbamate | n-Butyl isocyanate 24.8 g | 2,2,3,3,4,4,4-Hepta-fluorobutanol 50.1 g | Desmorapid Z 0.04 g | 60° C. | colourless solid |
| 7 | 2,2,3,3,4,4,5,5,6,6,7,7,8,8,9,9-Hexadecafluorononyl butylcarbamate | n-Butyl isocyanate 186 g | 2,2,3,3,4,4,5,5,6,6,7,7,8,8,9,9-Hexadecafluoro-nonanol 813 g | Desmorapid Z 0.50 g | 60° C. | colourless liquid |
| 8 | Bis(2,2,3,3,4,4,4-heptafluorobutyl)-(2,2,4-trimethylhexane-1,6-diyl) biscarbamate | 2,4,4-Trimethylhexane 1,6-diisocyanate (TMDI) 6.88 g | 2,2,3,3,4,4,4-Hepta-fluorobutanol 13.1 g | Desmorapid Z 0.01 g | 60° C. | colourless liquid |
| 9 | Bis(2,2,3,3,4,4,4-heptafluorobutyl)-[4-({[(2,2,3,3,4,4,4-heptafluorobutoxy) carbonyl]amino}methyl) octane-1,8-diyl] biscarbamate | 1,8-Diisocyanato-4-(iso-cyanatomethyl) octane (TIN) 5.91 g | 2,2,3,3,4,4,4-Hepta-fluorobutanol 14.1 g | Desmorapid Z 0.01 g | 60° C. | colourless oil |
| 10 | 2,2,3,3,4,4,5,5,5-Nonafluoropentyl butylcarbamate | n-Butyl isocyanate 4.25 g | 2,2,3,3,4,4,5,5,5-Nona-fluoropentan-1-ol 10.7 g | Desmorapid Z 0.02 g | 70° C. | colourless liquid |
| 11 | Bis(2,2,3,3,4,4,5,5,5-nonafluoropentyl)-(2,2,4-trimethylhexane-1,6-diyl) biscarbamate | 2,4,4-Trimethylhexane 1,6-diisocyanate (TMDI) 4.43 g | 2,2,3,3,4,4,5,5,5-Nona-fluoropentan-1-ol 10.6 g | Desmorapid Z 0.02 g | 70° C. | colourless liquid |
| 12 | 2,2,3,3,4,4,5,5,5-Nonafluoropentyl hexylcarbamate | n-Hexyl isocyanate 5.05 g | 2,2,3,3,4,4,5,5,5-Nona-fluoropentan-1-ol 9.94 g | Desmorapid Z 0.02 g | 70° C. | colourless liquid |
| 13 | 2,2,3,3,4,4,5,5,5-Nonafluoropentyl propan-2-yl carbamate | i-Propyl isocyanate 3.81 g | 2,2,3,3,4,4,5,5,5-Nona-fluoropentan-1-ol 11.2 g | Desmorapid Z 0.02 g | 70° C. | colourless liquid |
| 14 | 2,2,3,3,4,4,5,5,6,6,6-Undecafluorohexyl butylcarbamate | n-Butyl isocyanate 3.72 g | 2,2,3,3,4,4,5,5,6,6,6-Undecafluorohexan-1-ol 11.3 g | Desmorapid Z 0.02 g | 70° C. | colourless liquid |

TABLE 2-continued

Preparation and characterization of Examples 2-35

| Example | Name | Isocyanate and amount | Alcohol and amount | Catalyst and amount | Temp [° C.] | Description |
|---|---|---|---|---|---|---|
| 15 | Bis(2,2,3,3,4,4,5,5,6,6,6-undecafluorohexyl)-(2,2,4-trimethylhexane-1,6-diyl) biscarbamate | 2,4,4-Trimethylhexane 1,6-diisocyanate (TMDI) 3.88 g | 2,2,3,3,4,4,5,5,6,6,6-Undecafluorohexan-1-ol 11.1 g | Desmorapid Z 0.02 g | 70° C. | colourless oil |
| 16 | 2,2,3,3,4,4,5,5,6,6,6-Undecafluorohexyl hexylcarbamate | n-Hexyl isocyanate 4.46 g | 2,2,3,3,4,4,5,5,6,6,6-Undecafluorohexan-1-ol 10.5 g | Desmorapid Z 0.02 g | 70° C. | colourless liquid |
| 17 | Bis(2,2,3,3,4,4,5,5,6,6,7,7-dodecafluoroheptyl)-(2,2,4-trimethylhexane-1,6-diyl) biscarbamate | 2,4,4-Trimethylhexane 1,6-diisocyanate (TMDI) 3.60 g | 2,2,3,3,4,4,5,5,6,6,7,7-Dodecafluoroheptan-1-ol 11.4 g | Desmorapid Z 0.02 g | 70° C. | colourless oil |
| 18 | 2,2,3,3,4,4,5,5,6,6,7,7-Dodecafluoroheptyl hexylcarbamate | n-Hexyl isocyanate 4.15 g | 2,2,3,3,4,4,5,5,6,6,7,7-Dodecafluoroheptan-1-ol 10.8 g | Desmorapid Z 0.02 g | 70° C. | colourless liquid |
| 19 | 2,2,3,3,4,4,5,5,6,6,7,7-Dodecafluoroheptyl propan-2-ylcarbamate | i-Propyl isocyanate 3.06 g | 2,2,3,3,4,4,5,5,6,6,7,7-Dodecafluoroheptan-1-ol 11.93 g | Desmorapid Z 0.02 g | 70° C. | colourless liquid |
| 20 | 2,2,3,3,4,4,5,5,6,6,7,7-Dodecafluoroheptyl cyclohexylcarbamate | Cyclohexyl isocyanate 4.10 g | 2,2,3,3,4,4,5,5,6,6,7,7-Dodecafluoroheptan-1-ol 10.9 g | Desmorapid Z 0.02 g | 70° C. | colourless liquid |
| 21 | 2,2,3,4,4,4-Hexafluorobutyl butylcarbamate | n-Butyl isocyanate 5.28 g | 2,2,3,4,4,4-Hexafluorobutan-1-ol 9.71 g | Desmorapid Z 0.02 g | 70° C. | colourless liquid |
| 22 | 2,2,3,4,4,4-Hexafluorobutyl hexylcarbamate | n-Hexyl isocyanate 6.16 g | 2,2,3,4,4,4-Hexafluoro-butan-1-ol 8.83 g | Desmorapid Z 0.02 g | 70° C. | colourless liquid |
| 23 | 2,2,3,4,4,4-Hexafluorobutyl propan-2-ylcarbamate | i-Propyl isocyanate 4.77 g | 2,2,3,4,4,4-Hexafluoro-butan-1-ol 10.2 g | Desmorapid Z 0.02 g | 70° C. | colourless oil |
| 24 | 2,2,3,3,4,4,5,5-Octafluoropentyl butylcarbamate | n-Butyl isocyanate 4.48 g | 2,2,3,3,4,4,5,5-Octa-fluoropentan-1-ol 10.5 g | Desmorapid Z 0.02 g | 70° C. | colourless liquid |
| 25 | Bis(2,2,3,3,4,4,5,5-octafluoropentyl)-{4-[({[(2,2,3,3,4,4,5,5-octafluoropentyl)-oxy]carbonyl}amino)methyl] octane 1,8-diyl biscarbamate | 1,8-Diisocyanato-4-(isocyanatomethyl) octane (TIN) 3.98 g | 2,2,3,3,4,4,5,5-Octa-fluoropentan-1-ol 11.0 g | Desmorapid Z 0.02 g | 70° C. | colourless oil |
| 26 | Bis(2,2,3,3,4,4,5,5-octafluoropentyl)-(2,2,4-trimethylhexane-1,6-diyl) biscarbamate | 2,4,4-Trimethylhexane 1,6-diisocyanate (TMDI) 4.67 g | 2,2,3,3,4,4,5,5-Octa-fluoropentan-1-ol 10.3 g | Desmorapid Z 0.02 g | 70° C. | colourless oil |
| 27 | 2,2,3,3,4,4,5,5-Octafluoropentyl propan-2-ylcarbamate | i-Propyl isocyanate 4.02 g | 2,2,3,3,4,4,5,5-Octa-fluoropentan-1-ol 10.9 g | Desmorapid Z 0.02 g | 70° C. | colourless liquid |
| 28 | 2,2,3,3,4,4,5,5-Octafluoropentyl cyclohexylcarbamate | Cyclohexyl isocyanate 5.25 g | 2,2,3,3,4,4,5,5-Octa-fluoropentan-1-ol 9.73 g | Desmorapid Z 0.02 g | 70° C. | colourless liquid |
| 29 | Bis(2,2,3,3-tetrafluoropropyl)-[4-({[(2,2,3,3-tetrafluoropropoxy)carbonyl]amino}methyl)octan-1,8-diyl] biscarbamate | 1,8-Diisocyanato-4-(isocyanatomethyl) octane (TIN) 5.83 g | 2,2,3,3-Tetrafluoro-1-propanol 9.16 g | Desmorapid Z 0.02 g | 70° C. | colourless oil |
| 30 | Bis(2,2,3,3-tetrafluoropropyl)-(2,2,4-trimethylhexane-1,6-diyl) biscarbamate | 2,4,4-Trimethylhexane 1,6-diisocyanate (TMDI) 6.64 g | 2,2,3,3-Tetrafluoro-1-propanol 8.35 g | Desmorapid Z 0.02 g | 70° C. | colourless liquid |
| 31 | 2,2,3,3-Tetrafluoropropyl propan-2-ylcarbamate | i-Propyl isocyanate 5.87 g | 2,2,3,3-Tetrafluoro-propan-1-ol 9.11 g | Desmorapid Z 0.02 g | 70° C. | colourless liquid |
| 32 | Ethyl hexylcarbamate | n-Hexyl isocyanate 36.7 g | Ethanol 13.3 g | Desmorapid Z 0.02 g | 60° C. | colourless liquid |
| 33 | iso-Propyl hexylcarbamate | n-Hexyl isocyanate 34.0 g | iso-Propanol 16.0 g | Desmorapid Z 0.02 g | 60° C. | colourless liquid |
| 34 | 3-Ethyl butylcarbamate | n-Butyl isocyanate 34.1 g | Ethanol 15.9 g | Desmorapid Z 0.02 g | 60° C. | colourless liquid |
| 35 | iso-Propyl butylcarbamate | n-Butyl isocyanate 31.1 g | iso-Propanol 18.9 g | Desmorapid Z 0.02 g | 60° C. | colourless liquid |

Estimation of the Refractive Index ($n_D^{20}$) and of the Volatility (TGA95) of 2,2,2-trifluoroethyl butylcarbamate—(Example 1)

The three-dimensional structure of the abovementioned compound (Example 1) was generated and preoptimized with the aid of the graphic user interface of the molecular modelling package Materials Studio of Accelrys. This pre-optimized structure was then used as input for the conformer analysis, for which a Monte Carlo algorithm was used, which, in each case starting from the conformer generated just beforehand, changes all dihedral angles within the molecule according to the random principle. In this way, 1000 random conformers were generated and directly pre-optimized. In the procedure, all conformers which have a relative energy of >8.37 kJ/mol were directly discarded.

After this procedure, all 90 conformers obtained was subsequently optimized using a more stringent convergence criterion and then subjected to a similarity analysis, very similar conformers being discarded. The remaining 34 conformers were then optimized geometrically using the quantum chemistry package TURBOMOLE with the aid of the density functional theory. The B-P86 density functional and the triple ζ valence basis set TZVP, which was taken from the TURBOMOLE basis set library, were used and the COSMO option, using the optimized COSMO radii, was switched on.

For the 22 conformers whose relative DFT/COSMO Energy was <8 kJ/mol, the individual descriptors $V_i$, $A_i$ and $M^2_i$ were subsequently calculated according to steps e and f of the method according to the invention. For this purpose, the COSMOtherm of COSMOlogic was used. The results are listed in Table 3.

TABLE 3

| Conformer | Rel. energy in kJ/mol | Boltzmann Weight in % | V(Å$^3$) | A(Å$^2$) | M$^2$ |
|---|---|---|---|---|---|
| 1 | 0.00 | 15.92 | 224.534 | 224.129 | 69.717 |
| 2 | 0.14 | 15.02 | 224.692 | 224.472 | 69.698 |
| 3 | 0.46 | 13.21 | 223.745 | 228.546 | 74.656 |
| 4 | 0.95 | 10.86 | 222.437 | 228.836 | 74.314 |
| 5 | 1.80 | 7.70 | 224.267 | 226.684 | 73.407 |
| 6 | 1.90 | 7.39 | 224.614 | 226.738 | 73.401 |
| 7 | 3.86 | 3.35 | 222.143 | 224.595 | 74.151 |
| 8 | 3.96 | 3.22 | 223.430 | 227.027 | 74.845 |
| 9 | 4.09 | 3.06 | 224.181 | 220.790 | 73.732 |
| 10 | 4.24 | 2.88 | 226.841 | 218.562 | 73.464 |
| 11 | 5.07 | 2.06 | 222.067 | 227.356 | 72.800 |
| 12 | 5.08 | 2.05 | 224.635 | 224.359 | 72.785 |
| 13 | 5.35 | 1.84 | 225.926 | 217.658 | 76.949 |
| 14 | 5.58 | 1.68 | 227.028 | 216.153 | 72.131 |
| 15 | 6.32 | 1.24 | 222.207 | 226.866 | 74.032 |
| 16 | 6.39 | 1.21 | 224.162 | 220.368 | 71.597 |
| 17 | 6.97 | 0.95 | 224.831 | 226.248 | 75.008 |
| 18 | 7.55 | 0.76 | 224.889 | 222.006 | 71.440 |
| 19 | 7.60 | 0.74 | 225.386 | 223.325 | 75.264 |
| 20 | 7.72 | 0.71 | 225.336 | 225.147 | 74.730 |
| 21 | 7.88 | 0.66 | 221.676 | 224.815 | 72.557 |
| 22 | 7.88 | 0.66 | 226.532 | 216.022 | 73.523 |

This gives the following as Boltzmann-weighted mean values:
A=225.308 Å$^2$, V=224.137 Å$^3$, M$^2$=72.609

It results in the values 85.0° C. and 1.197 g/mol for the volatility (TGA95) and the density.

The molar polarizability was estimated as 40.310 m$^3$/mol with the aid of the QSPR approach published in 1986 by Crippen and implemented in the Materials Studio QSAR module, which, in combination with the density, results in a refractive index of ($n_D^{20}$)=1.3999. The substance, with a TGA95 value of 85.0° C. and a refractive index of 1.3999, is therefore not suitable overall in the context of the selection method according to the invention as an additive for photopolymer formulations since its estimated volatility is clearly too high. As shown by the comparison with experimental values, this evaluation is correct.

The volatilities and refractive indices of Examples 2-39 were calculated in a manner analogous to that of Example 1 and the results were summarized in Table 4. A further 30 fluorinated urethanes (Examples 2-31), 4 unfluorinated urethanes (Examples 32-35) and four commercial plasticizers (Examples 36-39) are contained therein.

TABLE 4

Comparison of estimated and experimental refractive indices and TGA95 values.

| Example | Name | V/Å$^3$ | A/Å$^2$ | M$^2$ | M/ (g/mol) | MP/ (m$^3$/mol) | ρ (QSPR) | ($n_D^{20}$) (QSPR) | TGA95 (QSPR) | ($n_D^{20}$) (Exp.) | TGA95 (Exp.) |
|---|---|---|---|---|---|---|---|---|---|---|---|
| 2 | 2,2,2-Trifluoroethyl hexylcarbamate | 266.609 | 268.162 | 76.273 | 227.23 | 49.51 | 1.146 | 1.4136 | 72.2 | 1.3984 | 72.5 |
| 3 | 2,2,3,3-Tetrafluoropropyl butylcarbamate | 254.440 | 253.494 | 94.734 | 231.19 | 44.09 | 1.241 | 1.3893 | 86.5 | 1.3879 | 71.6 |
| 4 | Bis(2,2,2-trifluoroethyl)-(2,2,4-trimethylhexane-1,6-diyl) biscarbamate | 449.384 | 412.813 | 142.624 | 410.35 | 83.03 | 1.285 | 1.4333 | 135.5 | 1.4202 | 167.1 |
| 5 | Bis(2,2,2-trifluoroethyl)-[4-({[(2,2,2-trifluoroethoxy)carbonyl]amino}methyl)-octane-1,8-diyl] biscarbamate | 571.236 | 540.825 | 214.491 | 551.40 | 103.39 | 1.384 | 1.4322 | 172.5 | 1.4213 | 174.9 |
| 6 | 2,2,3,3,4,4,4-Heptafluorobutyl butylcarbamate | 299.099 | 285.161 | 71.344 | 299.19 | 49.65 | 1.372 | 1.3727 | 75.5 | 1.3625 | 69.8 |

TABLE 4-continued

Comparison of estimated and experimental refractive indices and TGA95 values.

| Example | Name | V/Å$^3$ | A/Å$^2$ | M$^2$ | M/ (g/mol) | MP/ (m$^3$/mol) | ρ (QSPR) | ($n_D^{20}$) (QSPR) | TGA95 (QSPR) | ($n_D^{20}$) (Exp.) | TGA95 (Exp.) |
|---|---|---|---|---|---|---|---|---|---|---|---|
| 7 | 2,2,3,3,4,4,5,5,6,6,7,7,8,8,9,9-Hexadecafluorononyl butylcarbamate | 476.888 | 415.268 | 92.904 | 531.23 | 72.10 | 1.569 | 1.3459 | 116.6 | 1.3555 | 111.8 |
| 8 | Bis(2,2,3,3,4,4,4-heptafluorobutyl)-(2,2,4-trimethylhexane-1,6-diyl) biscarbamate | 606.335 | 522.310 | 136.852 | 610.38 | 101.71 | 1.432 | 1.3930 | 151.5 | 1.3887 | 139.1 |
| 9 | Bis(2,2,3,3,4,4,4-heptafluorobutyl)-[4-({[(2,2,3,3,4,4,4-heptafluorobutoxy)carbonyl]amino}methyl)octane-1,8-diyl] biscarbamate | 813.142 | 689.703 | 193.478 | 851.44 | 131.40 | 1.517 | 1.3846 | 191.3 | 1.3876 | 159.7 |
| 10 | 2,2,3,3,4,4,5,5,5-Nonafluoropentyl butylcarbamate | 336.687 | 311.927 | 73.341 | 349.19 | 54.31 | 1.433 | 1.3640 | 83.5 | 1.3580 | 72.8 |
| 11 | Bis(2,2,3,3,4,4,5,5,5-nonafluoropentyl)-(2,2,4-trimethylhexane-1,6-diyl) biscarbamate | 683.549 | 574.484 | 135.816 | 710.40 | 111.04 | 1.484 | 1.3807 | 160.5 | 1.3820 | 157 |
| 12 | 2,2,3,3,4,4,5,5,5-Nonafluoropentyl hexylcarbamate | 379.492 | 352.267 | 73.741 | 377.25 | 63.52 | 1.369 | 1.3780 | 89.9 | 1.3690 | 83.5 |
| 13 | 2,2,3,3,4,4,5,5,5-Nonafluoropentyl propan-2-ylcarbamate | 315.705 | 289.954 | 70.340 | 335.17 | 49.61 | 1.469 | 1.3541 | 79.0 | 1.3497 | 58.5 |
| 14 | 2,2,3,3,4,4,5,5,6,6,6-Undecafluorohexyl butylcarbamate | 374.581 | 335.864 | 68.869 | 399.20 | 58.98 | 1.479 | 1.3560 | 87.7 | 1.3538 | 82.6 |
| 15 | Bis(2,2,3,3,4,4,5,5,6,6,6-undecafluorohexyl)-(2,2,4-trimethyl-hexane-1,6-diyl) biscarbamate | 757.048 | 613.121 | 134.098 | 810.41 | 120.38 | 1.536 | 1.3736 | 169.4 | 1.3750 | 152.7 |
| 16 | 2,2,3,3,4,4,5,5,6,6,6-Undecafluorohexyl hexylcarbamate | 416.853 | 379.371 | 73.759 | 427.25 | 68.18 | 1.419 | 1.3704 | 96.4 | 1.3640 | 90 |
| 17 | Bis(2,2,3,3,4,4,5,5,6,6,7,7-dodecafluoroheptyl)-(2,2,4-trimethylhexane-1,6-diyl) biscarbamate | 811.336 | 671.039 | 176.795 | 874.44 | 127.93 | 1.560 | 1.3739 | 187.5 | 1.3839 | 158.6 |
| 18 | 2,2,3,3,4,4,5,5,6,6,7,7-Dodecafluoroheptyl hexylcarbamate | 445.778 | 401.101 | 94.859 | 459.27 | 71.96 | 1.440 | 1.3690 | 112.1 | 1.3716 | 117.6 |
| 19 | 2,2,3,3,4,4,5,5,6,6,7,7-Dodecafluoro-heptylpropan-2-yl carbamate | 381.492 | 338.779 | 91.463 | 417.19 | 58.05 | 1.534 | 1.3470 | 103.0 | 1.3563 | 93.3 |
| 20 | 2,2,3,3,4,4,5,5,6,6,7,7-Dodecafluoroheptyl cyclohexylcarbamate | 430.049 | 369.790 | 83.268 | 457.25 | 69.90 | 1.491 | 1.3731 | 105.9 | 1.3830 | 123.7 |
| 21 | 2,2,3,4,4,4-Hexafluorobutyl butylcarbamate | 291.826 | 273.825 | 90.643 | 281.20 | 49.25 | 1.332 | 1.3829 | 90.0 | 1.3775 | 73.8 |
| 22 | 2,2,3,4,4,4-Hexafluorobutyl hexylcarbamate | 335.639 | 313.390 | 92.270 | 309.25 | 58.45 | 1.271 | 1.3959 | 95.5 | 1.3876 | 89.5 |
| 23 | 2,2,3,4,4,4-Hexafluorobutyl propan-2-ylcarbamate | 269.738 | 259.029 | 91.749 | 267.17 | 44.54 | 1.368 | 1.3733 | 87.7 | 1.3682 | 71.5 |
| 24 | 2,2,3,3,4,4,5,5-Octafluoropentyl butylcarbamate | 330.134 | 303.188 | 88.913 | 331.20 | 53.42 | 1.393 | 1.3674 | 93.7 | 1.3731 | 80.5 |

TABLE 4-continued

Comparison of estimated and experimental refractive indices and TGA95 values.

| Example | Name | V/Å³ | A/Å² | M² | M/ (g/mol) | MP/ (m³/mol) | ρ (QSPR) | $(n_D^{20})$ (QSPR) | TGA95 (QSPR) | $(n_D^{20})$ (Exp.) | TGA95 (Exp.) |
|---|---|---|---|---|---|---|---|---|---|---|---|
| 25 | Bis(2,2,3,3,4,4,5,5-octafluoropentyl)-{4-[({[(2,2,3,3,4,4,5,5-octafluoropentyl)-oxy]carbonyl}amino)methyl]octane-1,8-diyl} biscarbamate | 895.878 | 763.826 | 254.799 | 947.50 | 142.73 | 1.552 | 1.3840 | 215.0 | 1.3955 | 172.5 |
| 26 | Bis(2,2,3,3,4,4,5,5-octafluoropentyl)-(2,2,4-trimethylhexane-1,6-diyl) biscarbamate | 667.015 | 566.787 | 174.890 | 674.42 | 109.26 | 1.457 | 1.3880 | 172.4 | 1.3971 | 163.9 |
| 27 | 2,2,3,3,4,4,5,5-Octafluoropentyl propan-2-ylcarbamate | 308.600 | 286.261 | 90.842 | 317.18 | 48.72 | 1.429 | 1.3577 | 92.3 | 1.3654 | 74.4 |
| 28 | 2,2,3,3,4,4,5,5-Octafluoropentyl-cyclohexylcarbamate | 355.202 | 319.977 | 87.653 | 357.24 | 60.56 | 1.400 | 1.3905 | 96.7 | 1.3977 | 110.5 |
| 29 | Bis(2,2,3,3-tetrafluoropropyl)-[4-({[(2,2,3,3-tetrafluoropropoxy)-carbonyl]amino}methyl)octane-1,8-diyl] biscarbamate | 668.003 | 606.741 | 275.686 | 647.45 | 114.73 | 1.417 | 1.4162 | 202.8 | 1.4240 | 197.9 |
| 30 | Bis(2,2,3,3-tetrafluoropropyl)-(2,2,4-trimethylhexane-1,6-diyl) biscarbamate | 517.127 | 461.959 | 184.103 | 474.39 | 90.59 | 1.313 | 1.4155 | 161.6 | 1.4229 | 185.3 |
| 31 | 2,2,3,3-Tetrafluoropropyl propan-2-ylcarbamate | 234.335 | 231.845 | 93.129 | 217.16 | 39.38 | 1.268 | 1.3770 | 85.2 | 1.3831 | 78.1 |
| 32 | Ethyl hexylcarbamate | 241.340 | 247.593 | 72.851 | 173.26 | 48.81 | 0.941 | 1.4431 | 65.5 | 1.4376 | 83.9 |
| 33 | iso-Propyl hexylcarbamate | 264.827 | 264.082 | 70.384 | 187.28 | 53.23 | 0.930 | 1.4413 | 67.9 | 1.4336 | 84.9 |
| 34 | 3 Ethyl butylcarbamate | 197.717 | 207.505 | 71.325 | 145.20 | 39.61 | 0.960 | 1.4367 | 59.2 | 1.4313 | 66.1 |
| 35 | iso-Propyl butylcarbamate | 220.538 | 224.943 | 68.619 | 159.23 | 44.03 | 0.946 | 1.4361 | 60.1 | 1.4284 | 63.9 |
| 36 | Propylene carbonate | 115.733 | 128.139 | 71.612 | 102.09 | 21.49 | 1.167 | 1.4059 | 64.3 | 1.4210 | 87 |
| 37 | Dimethyl adipate | 221.881 | 226.334 | 97.343 | 174.20 | 42.28 | 1.055 | 1.4256 | 86.5 | 1.4280 | 80.4 |
| 38 | Diethylene glycol diacetate | 231.636 | 242.845 | 113.550 | 190.19 | 43.90 | 1.110 | 1.4261 | 97.9 | 1.4300 | 99.1 |
| 39 | Triethyl citrate | 328.385 | 305.298 | 134.859 | 276.28 | 64.18 | 1.174 | 1.4575 | 123.9 | 1.4420 | 131 |

Comparison Between Experimental and Estimated TGA95 and Refractive Index Values

The comparison between the experimental refractive indices and TGA95 values of Examples 1-39 and those estimated by the selection method according to the invention (Table 4), which is illustrated in the correlation diagrams in FIG. 3 and FIG. 4, clearly show the suitability of the method. The refractive indices could be determined with a standard deviation of 0.0082, the maximum error over the total set, with an absolute value of 0.0155 for Example 39, likewise being very small. The standard deviation for the TGA95 values is 15.8° C., with an absolute maximum error of 42.5° C. for the fluorinated urethane of Example 25. However, this comparatively large error is not significant since both the experimental value of 172.5° C. and the estimated value of 215.0° C. are substantially above the suitability limit of 100° C. Thus, in spite of the error, the compound is correctly classed by the method according to the invention as being suitable as an additive for photopolymer formulations. In general, it may be stated that very large differences between predicted and experimental TGA95 typically occur in the case of comparatively high absolute values (typically >150° C.), which is attributable to incipient decomposition of the substances. This fact does not imply any limitation of the informative power of the selection method according to the invention since the threshold value for the suitability of the substance at 100° C. is typically well below the decomposition temperature of customary additive molecules.

Selection of the Example Molecules on the Basis of the Method According to the Invention The refractive indices of Examples 1-39 are all below 1.4600. In this case, the TGA95 estimated by the method according to the invention are therefore decisive regarding the suitability as additives in photopolymer formulations. All examples whose estimated volatility, according to TGA95, is greater than 100° C. are summarized in Table 5.

TABLE 5

Additives selected according to the invention.

| Example | $(n_D^{20})$ (QSPR) | TGA95 (QSPR) | $(n_D^{20})$ (Exp.) | TGA95 (Exp.) |
|---|---|---|---|---|
| 4 | 1.4333 | 135.5 | 1.4202 | 167.1 |
| 5 | 1.4322 | 172.5 | 1.4213 | 174.9 |
| 7 | 1.3459 | 116.6 | 1.3555 | 111.8 |
| 8 | 1.3930 | 151.5 | 1.3887 | 139.1 |
| 9 | 1.3846 | 191.3 | 1.3876 | 159.7 |
| 11 | 1.3807 | 160.5 | 1.3820 | 157.0 |

TABLE 5-continued

Additives selected according to the invention.

| Example | $(n_D^{20})$ (QSPR) | TGA95 (QSPR) | $(n_D^{20})$ (Exp.) | TGA95 (Exp.) |
|---|---|---|---|---|
| 15 | 1.3736 | 169.4 | 1.3750 | 152.7 |
| 17 | 1.3739 | 187.5 | 1.3839 | 158.6 |
| 18 | 1.3690 | 112.1 | 1.3716 | 117.6 |
| 19 | 1.3470 | 103.0 | 1.3563 | 93.3 |
| 20 | 1.3731 | 105.9 | 1.3830 | 123.7 |
| 25 | 1.3840 | 215.0 | 1.3955 | 172.5 |
| 26 | 1.3880 | 172.4 | 1.3971 | 163.9 |
| 29 | 1.4162 | 202.8 | 1.4240 | 197.9 |
| 30 | 1.4155 | 161.6 | 1.4229 | 185.3 |
| 39 | 1.4575 | 123.9 | 1.4420 | 131.0 |

Examples 7 and 17 which, owing to their low refractive indices and the sufficiently high volatility, should be very efficient are selected for an experimental investigation of the holographic activity. The compound 2 which, with an estimated volatility of 72.2° C., is substantially outside the limits of the method according to the invention is selected as a comparative example.

Preparation of the Photopolymer Formulation for the Production of Holographic Films Film Example 1

6.77 g of the polyol component prepared as described above were mixed with 4.00 g of phosphorothioyltris(oxybenzene-4,1-diylcarbamoyloxyethane-2,1-diyl) trisacrylate (urethane acrylate 1), 4.00 g of 2-({[3-(methylsulphanyl)phenyl]carbamoyl}oxy)propylprop-2-enoate (urethane acrylate 2) 3.00 g of 2,2,3,3,4,4,5,5,6,6,7,7,8,8,9,9-hexadecafluorononyl butylcarbamate (Example 7), 0.02 g of Fomrez UL 28 (urethanization catalyst, commercial product of Momentive Performance Chemicals, Wilton, Conn., USA), 0.30 g of CGI 909 (experimental product of Ciba Inc, Basle, Switzerland), 0.03 g of new methylene blue, 0.06 g of BYK 310 and 1.02 g of N-ethylpyrrolidone at 60° C. so that a clear solution was obtained. Thereafter, cooling to 30° C. was effected, 1.25 g of Desmodur® N3900 (commercial product of Bayer MaterialScience AG, Leverkusen, Germany, hexane diisocyanate-based polyisocyanate, proportion of iminooxadiazinedione at least 30%, NCO content: 23.5%) were added and mixing was effected again. The liquid material obtained is then applied by means of a knife coater to a 36 μm thick polyethylene terephthalate film and dried for 4.5 minutes at 80° C. in an air circulation dryer. Thereafter, the photopolymer layer is covered with a 40 μm thick polyethylene film and rolled up.

Film Example 2

6.77 g of the polyol component prepared as described above were mixed with 4.00 g of phosphorothioyltris(oxybenzene-4,1-diylcarbamoyloxyethane-2,1-diyl) trisacrylate (urethane acrylate 1), 4.00 g of 2-({[3-(methylsulphanyl)phenyl]carbamoyl}oxy)propylprop-2-enoate (urethane acrylate 2) 3.00 g of bis(2,2,3,3,4,4,5,5,6,6,7,7-dodecafluoroheptyl)-(2,2,4-trimethylhexane-1,6-diyl) biscarbamate (Example 17), 0.02 g of Fomrez UL 28 (urethanization catalyst, commercial product of Momentive Performance Chemicals, Wilton, Conn., USA), 0.30 g of CGI 909 (experimental product of Ciba Inc, Basle, Switzerland), 0.03 g of new methylene blue, 0.06 g of BYK 310 and 1.02 g of N-ethylpyrrolidone at 60° C. so that a clear solution was obtained. Thereafter, cooling to 30° C. was effected, 1.25 g of Desmodur® N3900 (commercial product of Bayer MaterialScience AG, Leverkusen, Germany, hexane diisocyanate-based polyisocyanate, proportion of iminooxadiazinedione at least 30%, NCO content: 23.5%) were added and mixing was effected again. The liquid material obtained is then applied by means of a knife coater to a 36 μm thick polyethylene terephthalate film and dried for 4.5 minutes at 80° C. in an air circulation dryer. Thereafter, the photopolymer layer is covered with a 40 μm thick polyethylene film and rolled up.

Comparative Film Example 1

6.77 g of the polyol component prepared as described above were mixed with 4.00 g of phosphorothioyltris(oxybenzene-4,1-diylcarbamoyloxyethane-2,1-diyl) trisacrylate (urethane acrylate 1), 4.00 g of 2-({[3-(methylsulphanyl)phenyl]carbamoyl}oxy)propylprop-2-enoate (urethane acrylate 2) 3.00 g of 2,2,2-trifluoroethyl butylcarbamate (Example 1), 0.02 g of Fomrez UL 28 (urethanization catalyst, commercial product of Momentive Performance Chemicals, Wilton, Conn., USA), 0.30 g of CGI 909 (experimental product of Ciba Inc, Basle, Switzerland), 0.03 g of new methylene blue, 0.06 g of BYK 310 and 1.02 g of N-ethylpyrrolidone at 60° C. so that a clear solution was obtained. Thereafter, cooling to 30° C. was effected, 1.25 g of Desmodur® N3900 (commercial product of Bayer MaterialScience AG, Leverkusen, Germany, hexane diisocyanate-based polyisocyanate, proportion of iminooxadiazinedione at least 30%, NCO content: 23.5%) were added and mixing was effected again. The liquid material obtained is then applied by means of a knife coater to a 36 μm thick polyethylene terephthalate film and dried for 4.5 minutes at 80° C. in an air circulation dryer. Thereafter, the photopolymer layer is covered with a 40 μm thick polyethylene film and rolled up.

TABLE 6

Holographic evaluation of film examples

| Film Example | Example, [% by weight] | Δn |
|---|---|---|
| 1 | 7.15 | 0.038 |
| 2 | 17.15 | 0.032 |
| Comparative film example | Example [% by weight] | Δn |
| 1 | 2.15 | 0.012 |

The values described by Δn were obtained at doses of 4-32 mJ/cm$^2$.

The values found for the holographic property Δn of the holographic media show that the additives selected by the method according to the invention are better suited for use in holographic photopolymer films.

The invention claimed is:

1. A method for preparing a photopolymer formulation comprising selecting at least one plasticizer by
   a) selecting a compound to be tested,
   b) carrying out a conformer analysis of the compound to be tested,
   c) generating an optimization of the geometry of all conformers with the aid of a force field method and the conformer space is then further reduced with the aid of a similarity analysis,
   d) effecting a quantum chemical optimization of the geometry of the conformers which are energetically most favourable according to the force field optimization with the use of the B-P86 density functional and a triple ζ valence basis set, and of the Conductor Like Screening Model (COSMO) in combination with the optimized COSMO radii or, if no optimized COSMO radii exists for a given element, with 1.17 times the Bondi valence radius, e) calculating the area (A) in Å$^2$ and the enclosed volume (V) in Å$^3$ of the three-dimensional COSMO shielding charge density surfaces of the conformers having the lowest energy, which are obtained as result of the quantum chemical optimization of the geometry, f) dividing into segments, the COSMO shielding charge density surfaces of the conformers having the lowest energy with the aid of a suitable software package, the mean surface shielding charge density (σ) of these segments are plotted in the form of a frequency distribution P(σ) and the second moments (M$^2$) of this distribution, defined according to the equation:

$$M^2 = 10 \cdot \sum_i P(\sigma_i) \cdot \sigma_i^2 \cdot \Delta\sigma$$

are determined, Δσ being the interval width of the discrete frequency distribution and the charge densities σ being stated in the unit e/nm$^2$, g) averaging the volumes, areas and second moments of all conformers considered according to their weight in the Boltzmann distribution on the basis of the energies obtained from the quantum chemical optimizations of the geometries, h) estimating the volatility of the substance according to the computational rule:

$$TGA95 \approx 207.015 \cdot \frac{M^2}{A} + 41.405 \cdot \sqrt[3]{V} - 253.2,$$

i) estimating the density of the compound at room temperature with the aid of the equation:

$$\rho = 0.89 \cdot \frac{M}{V \cdot N_A} - 0.2 \cdot \frac{A}{V} + 0.01 \cdot \sqrt{M^2}$$

ρ being the density of the pure substance in g/cm$^3$, M being the molar mass in g/mol, $N_A$ being the Avogadro number, A being the COSMO shielding charge density surface in Å$^2$, V being the volume in Å$^3$ enclosed by the surface and M$^2$ being the second moment of the surface shielding charge density frequency distribution, j) using the estimated density in order, with the aid of the Lorentz-Lorenz equation:

$$n_D = \sqrt{\frac{2 \cdot \frac{\rho \cdot MP}{M} + 1}{1 - \frac{\rho \cdot MP}{M}}},$$

to convert the molar polarizability (MP) estimated according to a QSPR approach as accurately as possible into a refractive index at 589 nm ($n_D^{20}$)

k) determining whether the volatility of the compound to be tested is >100° C. and the refractive index thereof is ≤1.4600, and providing a matrix polymer, a writing monomers and a photoinitiators, and preparing a photopolymer formulation by incorporating the compound to be tested as the at least one plasticizer into the photopolymer formulation.

2. The method according to claim 1, wherein, in step f), the suitable software package is the program COSMOtherm of COSMOlogic.

3. The method according to claim 1, wherein, in step d), a quantum chemical optimization of the geometry of the conformer having the lowest energy according to the force field optimization is effected.

4. The method according to claim 1, wherein, in step d), a quantum chemical optimization of the geometry of all conformers in an energy window of 0-4 kJ/mol according to the force field optimization is effected.

5. The method according to claim 1, wherein, in step d), a quantum chemical optimization of the geometry of all conformers in an energy window of 0-8 kJ/mol according to the force field optimization is effected.

6. The method according to claim 1, wherein, in step k), a check is carried out to determine whether the volatility of the compound to be tested is >120° C. and the refractive index thereof nD is ≤1.4500.

7. The method according to claim 1, wherein, in step k), a check is carried out to determine whether the volatility of the compound to be tested is >120° C. and the refractive index thereof nD is ≤1.4400.

8. The method according to claim 1, wherein, in step k), a check is carried out to determine whether the volatility of the compound to be tested is >120° C. and the refractive index thereof nD is ≤1.4300.

9. The method according to claim 1, wherein the at least one plasticizer comprises urethanes, and wherein the urethane is optionally substituted by at least one fluorine atom.

10. The method according to claim 9, wherein the urethanes have the formula (II)

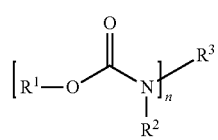

(II)

wherein n is from 1 to 8 and

R$^2$, R$^2$, R$^3$ represent, independently of one another, hydrogen or linear, branched, cyclic or heterocyclic organic radicals which are unsubstituted or optionally also substituted by heteroatoms.

11. The method according to claim 10, wherein at least one of the radicals R$^1$, R$^2$, R$^3$ is substituted by at least one fluorine atom.

* * * * *